(12) United States Patent
Chen et al.

(10) Patent No.: US 6,632,650 B1
(45) Date of Patent: Oct. 14, 2003

(54) GENES INVOLVED IN CYCLODODECANONE DEGRADATION PATHWAY

(75) Inventors: Mario W Chen, Chadds Ford, PA (US); Qiong Cheng, Wilmington, DE (US); Katharine Gibson, Wlmington, DE (US); Kristy Kostichka, Wilmington, DE (US); Stuart M Thomas, Wilmington, DE (US); Vasantha Nagarajan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 231 days.

(21) Appl. No.: 09/732,615

(22) Filed: Dec. 8, 2000

Related U.S. Application Data

(60) Provisional application No. 60/170,214, filed on Dec. 10, 1999.

(51) Int. Cl.[7] .............................. C12N 1/20; C12N 9/02; C12N 15/00; C07H 21/02; C07H 21/04
(52) U.S. Cl. ................................ 435/252.3; 435/320.1; 435/189; 435/252.31; 435/252.33; 435/253.32; 435/252.5; 435/252.8; 435/254.2; 536/23.2; 536/23.1
(58) Field of Search .......................... 435/189, 6, 252.3, 435/252.35, 320.1, 252.34, 252.5, 252.8, 253.32, 254.2; 536/23.2, 23.1, 23.7

(56) References Cited

U.S. PATENT DOCUMENTS

| | | | |
|---|---|---|---|
| 5,238,816 A | 8/1993 | Shigeyuki et al. | ............. 435/28 |
| 5,851,810 A | 12/1998 | Blanchard | ................... 435/189 |

OTHER PUBLICATIONS

Pahl et al. (J. Bacteriol, 180(23), 6396–6399, 1998, cited in the IDS), see the attached alignment.*
J. D. Schumacher and R. M. Fakoussa, Oxidation and Cleavage of alicyclic structures using bacterial biocatalysts, DGMK Tagungsber. (1997), 9704 Proceedings ICCS '97, vol. 3) 1583–1586.
J.D. Schumacher, et al., Appl. Microbiol. Biotechnol, 1999, 52:85–90.
Chen et al., J. Bacteriol. 170(2), 781–789 (1988).
Berger et al., J. Bacteriol. 180 (23), 6396–6399 (1998).
Cole, et al., Nature, 393(6685), 537–544 (1998).
PIR Accession No. A28500, Oct. 1999.
Genbank Accession No. AL022121, Jan. 1999.
Genbank Accession No. Z80226, Jun. 1998.
Genbank Accession No. AL096811.1, Jul. 1999.
Schumacher et al., Appl. Microbiol Biotechnol., Degradation of alicyclic molecules by *Rhodococcus ruber* CD4, 1999, 52:85–90.
Kulakova et al., "Hypothetical aldehyde dehydrogenase precursor" Swissport Sequence Data Base, Aug. 1, 1998, XP002167048.
Kulakova et al., "The plasmid–located haloalkane dehalogenase gene from *Rhodococcus rhodochrous* NCIMB 13064" Microbiology vol. 143, 1997, pp. 109–115 XP002167049.
Redenbach et al., "*Streptomyces coelicolor* cosmid 5G9" Embl Sequence Database, Sep. 13, 1999 XP002167037.
Redenbach et al., "Putative monooxgenase" Swissprot Sequence Data Base, May 1, 2000, XP002167038.
Redenbach et al., "*Streptomyces coelicolor* cosmid I30A", EMBL Sequence Database, Jul. 7, 1999 XP002167039.
Redenbach et al., "*Streptomyces coelicolor* cosmid 8B1" EMBL Sequence Database, Aug. 4, 2000, XP002167040.
Redenbach et al., "A set ordered cosmid and a detailed genetic and physical map for the 8Mb *Stereptomyces coelicolor* A3(2) chromosome", Molecular Microbiology vol. 21, No. 1, 1996 pp. 77–96 XP000876690.
Berger et al., "*Steptomyces chrysomallus* orfA, estA, cypA genes", EMBL Sequence Database, Sep. 22, 1992, XP002167041.
Cole et al., "*Mycobacterium tuberculosis* H37Rv complete genome; segment 36/162" EMBL Sequence Database, Sep. 18, 1996, XP002167043.
Mclean et al., "Hypothetical alcohol dehydrogenase–like protein CY369.06C" Swissprot Sequence Data Base, Nov. 1, 1998, XP002167044.
Cole et al., "Hypothetical 51.2 KDA protein" Swissprot Sequence Data Base, May 1, 1997, XP002167045.
Kulakova et al., "*Rhodococcus rhodochrous* plasmit pRTL1 insertion sequence IS112 . . . " EMBL Sequence Database, May 6, 1998, XP002167046.
Kulakova et al., "Hypothetical alcohol dehydrogenase", Swissprot Sequence Data Base, Aug. 1, 1998, XP002167047.

\* cited by examiner

*Primary Examiner*—Maryam Monshipouri

(57) ABSTRACT

A 10 kb gene cluster has been isolated from *Rhodococcus ruber* SC1 comprising genes encoding enzymes useful for the synthesis of dodecanoic diacid from cyclododecanone and other cyclic intermediates. The six specific open reading frames have been identified that are associated with dodecanoic diacid biosynthesis. In addition to the expected substrates the enzymes of the instant invention have moderate specificity for C11–C15 compounds.

11 Claims, 3 Drawing Sheets

SEQUENCE LISTING

<160> NUMBER OF SEQ ID NOS: 39

<210> SEQ ID NO 1
<211> LENGTH: 1812
<212> TYPE: DNA
<213> ORGANISM: Rhodococcus ruber
<220> FEATURE:

<400> SEQUENCE: 1

```
atgacgacga gcatcgaccg tgaagcgctc cggaggaagt atgcggaaga gcgcgacaag      60
cggatccgac cggacggaaa cgaccagtac attcgcctcg atcacgtgga cggctggtcg     120
catgacccgt acatgccgat cacgccccgc gaacccaagc tcgaccatgt gacgttcgca     180
ttcatcggcg gcggcttctc cggcctggtc accgccgcac gccttcgaga atccggagtc     240
gagagcgtcc gcatcatcga caaggccggc gacttcggtg gcgtctggta ctggaacaga     300
taccccggcg cgatgtgtga caccgcagcc atggtgtaca tgccgctgct cgaggaaacc     360
ggctacatgc ccaccgagaa gtacgcgcac ggcccggaga tcctcgaaca ctgccaacga     420
atcggcaaac actacgactt gtacgacgac gcgctgttcc acaccgaagt caccgacctg     480
gtctggcagg agcacgatca gcgctggcgg atctcgacga accgaggtga ccacttcacg     540
gcccaattcg tgggtatggg caccggccct ctgcacgtgg cgcagctgcc gggcatcccc     600
gggatcgaat cgttccgcgg caagtcgttc cacaccagtc gatgggacta cgactacacc     660
ggcggcgacg cgctgggcgc gccgatggac aagctcgcgg acaagcgcgt agcggtgatc     720
ggaaccggcg cgaccgcggt gcagtgcgtg cccgaactgg ccaagtactg cagggaactg     780
tacgtcgtcc aacgcacgcc gtcggcggtc gacgaacggg gaaaccaccc gatcgacgag     840
aagtggttcg cgcagatcgc gacacccggt tggcagaagc gctggctgga cagtttcacc     900
gccatctggg acggcgtgct caccgacccg agcgagttgg cgatcgaaca cgaggacctc     960
gtccaggacg ggtggaccgc gctcggccag aggatgcgtg cagccgtcgg atccgtgccg    1020
atcgagcagt actcgccgga aaatgtgcag cgggcactcg aggaggccga cgacgagcag    1080
atggagcgca tccgcgcccg cgtcgacgag atcgtcaccg atcccgccac tgccgcacag    1140
ctcaaggcct ggttccgtca gatgtgcaag cgaccgtgct tccatgacga ctacctgccg    1200
```

-continued

```
gcgttcaatc ggcccaacac acatctcgtc gacacgggcg gcaaaggggt ggagcgcatc    1260
accgagaacg gcgtggtcgt tgccggggtg gagtacgagg tggactgcat cgtctacgcc    1320
tccgggttcg aattcctcgg caccggctac accgaccgtg ccggattcga cccgacggga    1380
cgcgacgggg tcaagctgtc ggagcattgg gcgcagggca cgaacccct ccacggcatg     1440 cacacctacg gattccccaa cctgttcgtg ctccagttga tgcagggcgc agctctcgga    1500
tcgaacattc cccacaactt cgtcgaagcc gctcgcgtcg tcgctgcgat agtcgatcac    1560
gtgctgagca ccggcacatc cagcgtcgag acgacgaagg aggccgagca ggcgtgggtg    1620
cagcttctcc tcgaccacgg ccggccctc ggtaatcccg aatgcactcc gggctactac     1680
aacaacgaag gcaaacccgc cgaactgaag gatcggctca acgtcggcta tccggcaggc    1740
tcggcagcgt tcttccgcat gatggaccac tggcttgcgg ccggcagctt cgacggcctc    1800
accttccgct ga                                                        1812
```

<210> SEQ ID NO 2
<211> LENGTH: 603
<212> TYPE: PRT
<213> ORGANISM: Rhodococcus ruber
<220> FEATURE:

<400> SEQUENCE: 2

```
Met Thr Thr Ser Ile Asp Arg Glu Ala Leu Arg Arg Lys Tyr Ala Glu
  1               5                  10                  15

Glu Arg Asp Lys Arg Ile Arg Pro Asp Gly Asn Asp Gln Tyr Ile Arg
             20                  25                  30

Leu Asp His Val Asp Gly Trp Ser His Asp Pro Tyr Met Pro Ile Thr
         35                  40                  45

Pro Arg Glu Pro Lys Leu Asp His Val Thr Phe Ala Phe Ile Gly Gly
     50                  55                  60

Gly Phe Ser Gly Leu Val Thr Ala Ala Arg Leu Arg Glu Ser Gly Val
 65                  70                  75                  80

Glu Ser Val Arg Ile Ile Asp Lys Ala Gly Asp Phe Gly Gly Val Trp
                 85                  90                  95

Tyr Trp Asn Arg Tyr Pro Gly Ala Met Cys Asp Thr Ala Ala Met Val
            100                 105                 110

Tyr Met Pro Leu Leu Glu Glu Thr Gly Tyr Met Pro Thr Glu Lys Tyr
        115                 120                 125

Ala His Gly Pro Glu Ile Leu Glu His Cys Gln Arg Ile Gly Lys His
    130                 135                 140

Tyr Asp Leu Tyr Asp Asp Ala Leu Phe His Thr Glu Val Thr Asp Leu
145                 150                 155                 160

Val Trp Gln Glu His Asp Gln Arg Trp Arg Ile Ser Thr Asn Arg Gly
                165                 170                 175

Asp His Phe Thr Ala Gln Phe Val Gly Met Gly Thr Gly Pro Leu His
            180                 185                 190

Val Ala Gln Leu Pro Gly Ile Pro Gly Ile Glu Ser Phe Arg Gly Lys
        195                 200                 205

Ser Phe His Thr Ser Arg Trp Asp Tyr Asp Tyr Thr Gly Gly Asp Ala
    210                 215                 220

Leu Gly Ala Pro Met Asp Lys Leu Ala Asp Lys Arg Val Ala Val Ile
225                 230                 235                 240

Gly Thr Gly Ala Thr Ala Val Gln Cys Val Pro Glu Leu Ala Lys Tyr
                245                 250                 255
```

| | | | | | | | | | | | |
|---|---|---|---|---|---|---|---|---|---|---|---|
| Cys | Arg | Glu | Leu | Tyr | Val | Val | Gln | Arg | Thr | Pro | Ser | Ala | Val | Asp | Glu |
| | | 260 | | | | | 265 | | | | 270 | | | | |

Cys Arg Glu Leu Tyr Val Val Gln Arg Thr Pro Ser Ala Val Asp Glu
                260                     265                 270

Arg Gly Asn His Pro Ile Asp Glu Lys Trp Phe Ala Gln Ile Ala Thr
            275                     280                  285

Pro Gly Trp Gln Lys Arg Trp Leu Asp Ser Phe Thr Ala Ile Trp Asp
        290                 295                 300

Gly Val Leu Thr Asp Pro Ser Glu Leu Ala Ile Glu His Glu Asp Leu
305                 310                 315                 320

Val Gln Asp Gly Trp Thr Ala Leu Gly Gln Arg Met Arg Ala Ala Val
            325                 330                 335

Gly Ser Val Pro Ile Glu Gln Tyr Ser Pro Glu Asn Val Gln Arg Ala
            340                 345                 350

Leu Glu Glu Ala Asp Asp Glu Gln Met Glu Arg Ile Arg Ala Arg Val
            355                 360                 365

Asp Glu Ile Val Thr Asp Pro Ala Thr Ala Ala Gln Leu Lys Ala Trp
370                 375                 380

Phe Arg Gln Met Cys Lys Arg Pro Cys Phe His Asp Asp Tyr Leu Pro
385                 390                 395                 400

Ala Phe Asn Arg Pro Asn Thr His Leu Val Asp Thr Gly Lys Gly
                405                 410                 415

Val Glu Arg Ile Thr Glu Asn Gly Val Val Ala Gly Val Glu Tyr
            420                 425                 430

Glu Val Asp Cys Ile Val Tyr Ala Ser Gly Phe Glu Phe Leu Gly Thr
            435                 440                 445

Gly Tyr Thr Asp Arg Ala Gly Phe Asp Pro Thr Gly Arg Asp Gly Val
450                 455                 460

Lys Leu Ser Glu His Trp Ala Gln Gly Thr Arg Thr Leu His Gly Met
465                 470                 475                 480

His Thr Tyr Gly Phe Pro Asn Leu Phe Val Leu Gln Leu Met Gln Gly
                485                 490                 495

Ala Ala Leu Gly Ser Asn Ile Pro His Asn Phe Val Glu Ala Ala Arg
            500                 505                 510

Val Val Ala Ala Ile Val Asp His Val Leu Ser Thr Gly Thr Ser Ser
            515                 520                 525

Val Glu Thr Thr Lys Glu Ala Glu Gln Ala Trp Val Gln Leu Leu Leu
            530                 535                 540

Asp His Gly Arg Pro Leu Gly Asn Pro Glu Cys Thr Pro Gly Tyr Tyr
545                 550                 555                 560

Asn Asn Glu Gly Lys Pro Ala Glu Leu Lys Asp Arg Leu Asn Val Gly
                565                 570                 575

Tyr Pro Ala Gly Ser Ala Ala Phe Phe Arg Met Met Asp His Trp Leu
            580                 585                 590

Ala Ala Gly Ser Phe Asp Gly Leu Thr Phe Arg
            595                 600

<210> SEQ ID NO 3
<211> LENGTH: 1161
<212> TYPE: DNA
<213> ORGANISM: Rhodococcus ruber
<220> FEATURE:

<400> SEQUENCE: 3
atggatgaac cgaccatcgg cggattctgc gacgaccgat tcgccgccgt gcgccacatt      60
ttcgagcaga acgtcacgtc cggggaagaa ctcggcgccg ccctcgtcat cgacatcgac     120

-continued

```
ggagagacac gcgtcgacat ctggggagga ttccgcgacc aggcccggtc cacgccgtgg    180
accgaggaca ccatcgtcaa cgtgtggtcg agcacgaagt cggtactggc attggcggca    240
ctgatgctcg tcgacgccgg cgagctgaac ctcgacgcac ccgtcacgcg ctactggccc    300
gagttcgccg ccaacggcaa gagcgacatc gcggtacggc acatcctctc gcacacctcc    360
ggggtgtcgg gctgggaaca gcccttcgtc ctcgaggaca tgtacgactg ggacaagtcg    420
acgaccctgc tcgcgcagca agcaccatgg tggccggcgg gttcggccgc cggctaccac    480
gccaacaacc agggccacct catcggagaa atcgtccgcc gcatcaccgg ccgaccgttc    540
aaggagttcg tcaccacaca catcgccggt ccgctcgctg ccgacttcca gatcggcgcc    600
cgcgagaacg attggggccg taccgccgag atcgtcgcac cacccccctt cgacatcgat    660
ctcgccgcac tcgatcccga cagcgtcatg gtgaagacga tgacgggacc ggtagccgac    720
gcgaacgcgg ccaatactcc cggatggcgg cacgccgaca tgggagccct caacggtcac    780
ggcaacgcac gctcgctcgc tcggatcctc tcgaccatca cgctgggcgg tgagagcaac    840
ggcctccgcc tcctccacag cacctcgatc ggcaagattt tcgaagagca gaacaacgac    900
gtcgacctcg tcctcggtgt gccgttccgc cgcggcatcg gctacgcgct accgcgcccc    960
gacaccacgc cgagcatccc ggagggccgg atctgcttct ggggtggatg gggtggatcg   1020
atgacagtga tggacctcga ccgccggatg acgttcacct acgtgatgaa caagatgggg   1080
ccaggcatca tcggatcggc ccggagcgag cagtacctgc gcgccaccta cgatgccctc   1140
agcgagacgg tcaccgcgtg a                                             1161
```

<210> SEQ ID NO 4
<211> LENGTH: 386
<212> TYPE: PRT
<213> ORGANISM: Rhodococcus ruber
<220> FEATURE:

<400> SEQUENCE: 4

```
Met Asp Glu Pro Thr Ile Gly Gly Phe Cys Asp Asp Arg Phe Ala Ala
 1               5                  10                  15

Val Arg His Ile Phe Glu Gln Asn Val Thr Ser Gly Glu Glu Leu Gly
            20                  25                  30

Ala Ala Leu Val Ile Asp Ile Asp Gly Glu Thr Arg Val Asp Ile Trp
        35                  40                  45

Gly Gly Phe Arg Asp Gln Ala Arg Ser Thr Pro Trp Thr Glu Asp Thr
    50                  55                  60

Ile Val Asn Val Trp Ser Ser Thr Lys Ser Val Leu Ala Leu Ala Ala
65                  70                  75                  80

Leu Met Leu Val Asp Ala Gly Glu Leu Asn Leu Asp Ala Pro Val Thr
                85                  90                  95

Arg Tyr Trp Pro Glu Phe Ala Ala Asn Gly Lys Ser Asp Ile Ala Val
           100                 105                 110

Arg His Ile Leu Ser His Thr Ser Gly Val Ser Gly Trp Glu Gln Pro
       115                 120                 125

Phe Val Leu Glu Asp Met Tyr Asp Trp Asp Lys Ser Thr Thr Leu Leu
   130                 135                 140

Ala Gln Gln Ala Pro Trp Trp Pro Ala Gly Ser Ala Ala Gly Tyr His
145                 150                 155                 160

Ala Asn Asn Gln Gly His Leu Ile Gly Glu Ile Val Arg Arg Ile Thr
                165                 170                 175
```

-continued

Gly Arg Pro Phe Lys Glu Phe Val Thr Thr His Ile Ala Gly Pro Leu
                180                 185                 190

Ala Ala Asp Phe Gln Ile Gly Ala Arg Glu Asn Asp Trp Gly Arg Thr
            195                 200                 205

Ala Glu Ile Val Ala Pro Pro Phe Asp Ile Asp Leu Ala Ala Leu
        210                 215                 220

Asp Pro Asp Ser Val Met Val Lys Thr Met Thr Gly Pro Val Ala Asp
225                 230                 235                 240

Ala Asn Ala Ala Asn Thr Pro Gly Trp Arg His Ala Asp Met Gly Ala
                245                 250                 255

Leu Asn Gly His Gly Asn Ala Arg Ser Leu Ala Arg Ile Leu Ser Thr
                260                 265                 270

Ile Thr Leu Gly Gly Glu Ser Asn Gly Leu Arg Leu Leu His Ser Thr
            275                 280                 285

Ser Ile Gly Lys Ile Phe Glu Glu Gln Asn Asn Asp Val Asp Leu Val
        290                 295                 300

Leu Gly Val Pro Phe Arg Arg Gly Ile Gly Tyr Ala Leu Pro Arg Pro
305                 310                 315                 320

Asp Thr Thr Pro Ser Ile Pro Glu Gly Arg Ile Cys Phe Trp Gly Gly
                325                 330                 335

Trp Gly Gly Ser Met Thr Val Met Asp Leu Asp Arg Arg Met Thr Phe
            340                 345                 350

Thr Tyr Val Met Asn Lys Met Gly Pro Gly Ile Ile Gly Ser Ala Arg
        355                 360                 365

Ser Glu Gln Tyr Leu Arg Ala Thr Tyr Asp Ala Leu Ser Glu Thr Val
    370                 375                 380

Thr Ala
385

<210> SEQ ID NO 5
<211> LENGTH: 495
<212> TYPE: DNA
<213> ORGANISM: Rhodococcus ruber
<220> FEATURE:

<400> SEQUENCE: 5
atggggatcg agggtggcca gcaccgggtg ggcaccgcgg tactcgccca gagtgcgcag    60
gattttccgc agttttcggc ggttcgcgat ctgatgaccg ggatgtggtc cgacgggttc   120
ctggtcgaac ggagtgaact tgacagccat cacgtcatag cgcggcgcga gttcgacccc   180
gagctgctcg gcctcggcgt gagcgctgcg accgctgaga agcgttcttg ccacgaggta   240
cacggcgcca cgctcaccgt tggcgatggc ttcgcgctct gcctggtagg acgtggtgac   300
cgtactgagg atctcctgct gcagggtcag cagcttgcgc ccgatataac cgagtgcgtg   360
cgcgtcgtcg tcttgggccg cgtccgtgca ggcattccac aagacggtca tgccgttttg   420
ccagttgcgc aacaccaagg cgaggggaac cccttcgatc gctctgtctg cggcgatctc   480
ttgcaccatt cgtaa                                                    495

<210> SEQ ID NO 6
<211> LENGTH: 164
<212> TYPE: PRT
<213> ORGANISM: Rhodococcus ruber

<400> SEQUENCE: 6

Met Gly Ile Glu Gly Gly Gln His Arg Val Gly Thr Ala Val Leu Ala
 1               5                  10                  15

```
Gln Ser Ala Gln Asp Phe Pro Gln Phe Ser Ala Val Arg Asp Leu Met
             20                  25                  30

Thr Gly Met Trp Ser Asp Gly Phe Leu Val Glu Arg Ser Glu Leu Asp
         35                  40                  45

Ser His His Val Ile Ala Arg Arg Glu Phe Asp Pro Glu Leu Leu Gly
     50                  55                  60

Leu Gly Val Ser Ala Ala Thr Ala Glu Lys Arg Ser Cys His Glu Val
 65                  70                  75                  80

His Gly Ala Thr Leu Thr Val Gly Asp Gly Phe Ala Leu Cys Leu Val
                 85                  90                  95

Gly Arg Gly Asp Arg Thr Glu Asp Leu Leu Gln Gly Gln Gln Leu
            100                 105                 110

Ala Pro Asp Ile Thr Glu Cys Val Arg Val Val Leu Gly Arg Val
        115                 120                 125

Arg Ala Gly Ile Pro Gln Asp Gly His Ala Val Leu Pro Val Ala Gln
    130                 135                 140

His Gln Gly Glu Gly Asn Pro Phe Asp Arg Ser Val Cys Gly Asp Leu
145                 150                 155                 160

Leu His His Ser
```

<210> SEQ ID NO 7
<211> LENGTH: 1896
<212> TYPE: DNA
<213> ORGANISM: Rhodococcus ruber

<400> SEQUENCE: 7

| | | | | | |
|---|---|---|---|---|---|
| atgactgtta | agggaaagtc | ggcgacagcg | acgaccaagg | ctgcgaaccg | cgccgtgtct | 60 |
| gctcgcctgg | acttcgacga | caagacggcg | ttcgacgatg | cgcgccgtgg | cttcgtcgcc | 120 |
| acactcgatc | cgctggtgat | cagaaacgct | caaggtcatg | tcgtgtggga | cggcgatacc | 180 |
| tacgccttcc | tcgccgacga | ggcaccggac | acggtgaacc | cgagcctgtg | cgcatgtcg | 240 |
| caactacata | cgattcacgg | cctgttcaag | gtcgtcgacg | gcatctatca | ggtgcgcggc | 300 |
| ttcgacatct | ccaacatgac | tctggtcgag | ggcgacaccg | gatacgtcgt | catcgatccg | 360 |
| ctgacctcgg | ccgaatgcgc | ttcggcggcc | atggatctgg | tgcgcaggga | actcggtgac | 420 |
| cggccggtga | cggcgatcgt | ctacacccac | agccacgtcg | atcatttcgg | tggtgtgaaa | 480 |
| gggctcgtgt | cggaggcgga | catctccgcg | ggttccgtgc | ggatcgtcgc | gccgacgggg | 540 |
| ttcctggccc | acacggtcag | cgagaacgtc | tacgccggca | acgcgatgaa | ccgccgtgcg | 600 |
| cagtacatgc | acggcggcaa | gctgccgcac | gggccgagcg | gggtggtctc | ggccggtctc | 660 |
| ggcctcgggc | tctccaccgg | caccgtcacg | ctgctcgagc | ccaccgatta | cgtcaccgag | 720 |
| accggtcagg | aactcgtgct | cgacggggtg | cggttcgagt | ttcagtacac | gcccgacgcc | 780 |
| gaggcaccgg | ccgagatgaa | cttctacctg | cccgatttcc | gggcgctgtg | catggcggag | 840 |
| aacgtctctc | accacatgca | caacctgtac | accccccgcg | gcgcgcagat | tcgtgacgct | 900 |
| gccgcgtgga | gcgactacat | ccatgccgcg | atcgggctct | atgcgcaccg | gtcggacgtg | 960 |
| ctgttcatct | gtcaccactg | gccggtgtgg | ggtcggcaga | agctcaccga | cttcttggag | 1020 |
| cagcagcggg | acctgtaccg | ctacatccac | gacgagaccc | tgcgtctggc | cgcccacggc | 1080 |
| cacacgctgg | tcgagatcgc | cgaactgatc | gagctgcccg | agccgctggg | ctcgtcgtgg | 1140 |
| tcgagccgcg | gctactacgg | caccttgaac | cacaacgcca | aggcggtcta | tcagaagtac | 1200 |
| ctcggctggt | tcgacggcaa | tccggccacc | ttgcaccagc | atccaccggt | cgaggcgggt | 1260 |

```
aagcgctacg tcgaatacat gggcggagcc gacgccgtgc tgcgcaatgc gcgcaaatcg    1320
ttcgacgacg gggactaccg gtgggtggcc caggtggtca accatgtggt gttcgccgag    1380
ccggacaacc agcaggcacg ggaactgcag gcggacgcgc tcgaacagct cggctaccag    1440
gccgaatccg cttcgtggcg caacttctat ctcaccggtg cccaggaact gcgtcacggt    1500
gtggtggtgg agtcgacctc gttcgacacc tcggacgtgc tggccgcgat gacgacggac    1560
atgatgctca agtatctggc catccgtctg aacggaccga aggccgccgg ccgtgccttg    1620
cgggtcgacc tgcacgtgac cgacaccgac gagcgccggc tgctgcaggt gaccaacggt    1680
gtcctcgtcc acacggcgac gagcgcgccc caggatgcgg acgtgtcggt cgcgctcacc    1740
cgggccgcgc tcggatcgct gacgctcggc ggcacggccc tcgaccggtg cattgccgac    1800
ggcagcgtct cggtcggcgg caatgccgac gtgcttcgcg aactgttcgc gctgctcgac    1860
actttcgacc ggttcttcga catcgtcacc ccctga                             1896
```

<210> SEQ ID NO 8
<211> LENGTH: 631
<212> TYPE: PRT
<213> ORGANISM: Rhodococcus ruber

<400> SEQUENCE: 8

```
Met Thr Val Lys Gly Lys Ser Ala Thr Ala Thr Lys Ala Ala Asn
 1               5                  10                  15

Arg Ala Val Ser Ala Arg Leu Asp Phe Asp Asp Lys Thr Ala Phe Asp
             20                  25                  30

Asp Ala Arg Arg Gly Phe Val Ala Thr Leu Asp Pro Leu Val Ile Arg
         35                  40                  45

Asn Ala Gln Gly His Val Val Trp Asp Gly Asp Thr Tyr Ala Phe Leu
     50                  55                  60

Ala Asp Glu Ala Pro Asp Thr Val Asn Pro Ser Leu Trp Arg Met Ser
 65                  70                  75                  80

Gln Leu His Thr Ile His Gly Leu Phe Lys Val Val Asp Gly Ile Tyr
                 85                  90                  95

Gln Val Arg Gly Phe Asp Ile Ser Asn Met Thr Leu Val Glu Gly Asp
            100                 105                 110

Thr Gly Tyr Val Val Ile Asp Pro Leu Thr Ser Ala Glu Cys Ala Ser
        115                 120                 125

Ala Ala Met Asp Leu Val Arg Arg Glu Leu Gly Asp Arg Pro Val Thr
    130                 135                 140

Ala Ile Val Tyr Thr His Ser His Val Asp His Phe Gly Gly Val Lys
145                 150                 155                 160

Gly Leu Val Ser Glu Ala Asp Ile Ser Ala Gly Ser Val Arg Ile Val
                165                 170                 175

Ala Pro Thr Gly Phe Leu Ala His Thr Val Ser Glu Asn Val Tyr Ala
            180                 185                 190

Gly Asn Ala Met Asn Arg Arg Ala Gln Tyr Met His Gly Gly Lys Leu
        195                 200                 205

Pro His Gly Pro Ser Gly Val Val Ser Ala Gly Leu Gly Leu Gly Leu
    210                 215                 220

Ser Thr Gly Thr Val Thr Leu Leu Glu Pro Thr Asp Tyr Val Thr Glu
225                 230                 235                 240

Thr Gly Gln Glu Leu Val Leu Asp Gly Val Arg Phe Glu Phe Gln Tyr
                245                 250                 255
```

```
Thr Pro Asp Ala Glu Pro Ala Glu Met Asn Phe Tyr Leu Pro Asp
            260                 265                 270

Phe Arg Ala Leu Cys Met ala Glu Asn Val Ser His His Met His Asn
            275                 280                 285

Leu Tyr Thr Pro Arg Gly Ala Gln Ile Arg Asp Ala Ala Trp Ser
            290                 295                 300

Asp Tyr Ile His Ala Ala Ile Gly Leu Tyr Ala His Arg Ser Asp Val
305                 310                 315                 320

Leu Phe Ile Cys His His Trp Pro Val Trp Gly Arg Gln Lys Leu Thr
                325                 330                 335

Asp Phe Leu Glu Gln Gln Arg Asp Leu Tyr Arg Tyr Ile His Asp Glu
            340                 345                 350

Thr Leu Arg Leu Ala Ala His Gly His Thr Leu Val Glu Ile Ala Glu
            355                 360                 365

Leu Ile Glu Leu Pro Glu Pro Leu Gly Ser Ser Trp Ser Ser Arg Gly
            370                 375                 380

Tyr Tyr Gly Thr Leu Asn His Asn Ala Lys Ala Val Tyr Gln Lys Tyr
385                 390                 395                 400

Leu Gly Trp Phe Asp Gly Asn Pro Ala Thr Leu His Gln His Pro Pro
                405                 410                 415

Val Glu Ala Gly Lys Arg Tyr Val Glu Tyr Met Gly Gly Ala Asp Ala
            420                 425                 430

Val Leu Arg Asn Ala Arg Lys Ser Phe Asp Asp Gly Asp Tyr Arg Trp
            435                 440                 445

Val Ala Gln Val Val Asn His Val Val Phe Ala Glu Pro Asp Asn Gln
            450                 455                 460

Gln Ala Arg Glu Leu Gln Ala Asp Ala Leu Glu Gln Leu Gly Tyr Gln
465                 470                 475                 480

Ala Glu Ser Ala Ser Trp Arg Asn Phe Tyr Leu Thr Gly Ala Gln Glu
                485                 490                 495

Leu Arg His Gly Val Val Val Glu Ser Thr Ser Phe Asp Thr Ser Asp
            500                 505                 510

Val Leu Ala Ala Met Thr Thr Asp Met Met Leu Lys Tyr Leu Ala Ile
            515                 520                 525

Arg Leu Asn Gly Pro Lys Ala Ala Gly Arg Ala Leu Arg Val Asp Leu
            530                 535                 540

His Val Thr Asp Thr Asp Glu Arg Arg Leu Leu Gln Val Thr Asn Gly
545                 550                 555                 560

Val Leu Val His Thr Ala Thr Ser Ala Pro Gln Asp Ala Asp Val Ser
                565                 570                 575

Val Ala Leu Thr Arg Ala Ala Leu Gly Ser Leu Thr Leu Gly Gly Thr
            580                 585                 590

Ala Leu Asp Arg Cys Ile Ala Asp Gly Ser Val Ser Val Gly Gly Asn
            595                 600                 605

Ala Asp Val Leu Arg Glu Leu Phe Ala Leu Leu Asp Thr Phe Asp Arg
            610                 615                 620

Phe Phe Asp Ile Val Thr Pro
625                 630

<210> SEQ ID NO 9
<211> LENGTH: 1125
<212> TYPE: DNA
<213> ORGANISM: Rhodococcus ruber
```

<400> SEQUENCE: 9

```
atgaagacga aggcagccgt cctccgcgga gtcggtcagg actggcggat cgaggagatc      60
gagctcggcg atccggtccc cggcgaggtc caggtccgac tcgtggcgtc ggggatgtgc     120
cactccgatc accacctgcg gaccggtggt agcccgattc cgtttcccgt gatcggcggt     180
cacgaggggt cgggcatcgt caccaaggtc ggccccggtg tcacctctct cgtcgagggc     240
gatcatgtgg tgacggcgtt catcccggcg tgcggaacct gcgggccgtg ctcgcgggt      300
ctgcagaatc tgtgtgacga gggtgcgggg ctgctcaccg gtaggtccat ctccgacggg     360
acctaccggg cgagcgcgaa gggcgaacca ctggtgccga tgtgcctgct cggcacgttc     420
tctccgtaca tcaccgtcaa cgaggcgtcg ttggtgaaga tcgagaagga cattcccctc     480
gaagctgcgg cgctgctcgg ctgcggggtg gctaccgggt ggggttcggc gaccgcgatc     540
ggcggcacca aggtcggtga caccgtggtg gtcgtcggcg tcgagggtgt gggcatcaat     600
gccgtccagg gcgcggctgc cgccggggcg cgccacgtca tcgccgtcga cccggtggag     660
ttcaagcgac acatggccct cgcactcggt gcgacgcacg tgtatgcctc cctcgaagag     720
gcgatggaac cggtccggga cctgacctgg ggcctgatgc cggacgtgac ggtcttgacc     780
gtgggcgaca tcgaaggcga catcatccag ccggcgctga ccatcaccgc caaggccggc     840
caggtcgtcg tcaccgctat gggtgacgcg acaaagaacg aggtgacact caacctcttc     900
gagctgacgc tgctgcagaa cgggtccag gcgccatct tcggcggtgt ggggccgcgc       960
acccagatcc ccgctctcct gcatcactat cgcagcggtg cgctcaagct cgaggaactc    1020
gccaccaccg tctatcgcct cgaggacgtc aaccagggct acgacgacat gttggcgggc    1080
aagaacctgc gcggcatcat ccggtacacc gacgccgact tctga                    1125
```

<210> SEQ ID NO 10
<211> LENGTH: 374
<212> TYPE: PRT
<213> ORGANISM: Rhodococcus ruber

<400> SEQUENCE: 10

```
Met Lys Thr Lys Ala Ala Val Leu Arg Gly Val Gly Gln Asp Trp Arg
  1               5                  10                  15

Ile Glu Glu Ile Glu Leu Gly Asp Pro Val Pro Gly Glu Val Gln Val
             20                  25                  30

Arg Leu Val Ala Ser Gly Met Cys His Ser Asp His His Leu Arg Thr
         35                  40                  45

Gly Gly Ser Pro Ile Pro Phe Pro Val Ile Gly His Glu Gly Ser
     50                  55                  60

Gly Ile Val Thr Lys Val Gly Pro Gly Val Thr Ser Leu Val Glu Gly
 65                  70                  75                  80

Asp His Val Val Thr Ala Phe Ile Pro Ala Cys Gly Thr Cys Gly Pro
                 85                  90                  95

Cys Ser Arg Gly Leu Gln Asn Leu Cys Asp Glu Gly Ala Gly Leu Leu
            100                 105                 110

Thr Gly Arg Ser Ile Ser Asp Gly Thr Tyr Arg Ala Ser Ala Lys Gly
        115                 120                 125

Glu Pro Leu Val Pro Met Cys Leu Leu Gly Thr Phe Ser Pro Tyr Ile
    130                 135                 140

Thr Val Asn Glu Ala Ser Leu Val Lys Ile Glu Lys Asp Ile Pro Leu
145                 150                 155                 160
```

Glu Ala Ala Ala Leu Leu Gly Cys Gly Val Ala Thr Gly Trp Gly Ser
                165                 170                 175

Ala Thr Ala Ile Gly Gly Thr Lys Val Gly Asp Thr Val Val Val
            180                 185                 190

Gly Val Gly Gly Val Gly Ile Asn Ala Val Gln Gly Ala Ala Ala
        195                 200                 205

Gly Ala Arg His Val Ile Ala Val Asp Pro Val Glu Phe Lys Arg His
    210                 215                 220

Met Ala Leu Ala Leu Gly Ala Thr His Val Tyr Ala Ser Leu Glu Glu
225                 230                 235                 240

Ala Met Glu Pro Val Arg Asp Leu Thr Trp Gly Leu Met Ala Asp Val
                245                 250                 255

Thr Val Leu Thr Val Gly Asp Ile Glu Gly Asp Ile Ile Gln Pro Ala
            260                 265                 270

Leu Thr Ile Thr Ala Lys Ala Gly Gln Val Val Thr Ala Met Gly
        275                 280                 285

Asp Ala Thr Lys Asn Glu Val Thr Leu Asn Leu Phe Glu Leu Thr Leu
    290                 295                 300

Leu Gln Lys Arg Val Gln Gly Ala Ile Phe Gly Val Gly Pro Arg
305                 310                 315                 320

Thr Gln Ile Pro Ala Leu Leu His His Tyr Arg Ser Gly Ala Leu Lys
                325                 330                 335

Leu Glu Glu Leu Ala Thr Thr Val Tyr Arg Leu Glu Asp Val Asn Gln
            340                 345                 350

Gly Tyr Asp Asp Met Leu Ala Gly Lys Asn Leu Arg Gly Ile Ile Arg
        355                 360                 365

Tyr Thr Asp Ala Asp Phe
    370

<210> SEQ ID NO 11
<211> LENGTH: 1425
<212> TYPE: DNA
<213> ORGANISM: Rhodococcus ruber

<400> SEQUENCE: 11

```
atgaccgctg gccatttcac cgagctctac atcaacggtt cctgggttgc ctcgacaagc      60
aagacggtga tcgaggtgct caaccccgca accgaagagg tgatcgggac tgtcccggac     120
gggaccgcag cagatgtgga cgcggcggtg ccgctgccc gggccgcgtt cgacggctgg      180
gcgagcacac cggtcgacaa cgcgcgcag tacctacggg ccatcgccgc cggcatcgcc      240
gaccgcagcg acgagctggc acgcaccatc tctgccgaga tgggcgctcc gctgtcgttt     300
gcccaggcca tgcaggtgcc cctgccgatc aacagcttct cgcatgcagc ggccgtggcg     360
gagagcttcc cgttcgaacg caccgagggc tcatcggtga tcgtgcggga accgatcggg     420
gtggtggggg cgatcacccc gtggaactat cccctgcacc agatcgccgc gaaggtcgcc     480
tacgccctcg ccgccggcaa caccatcgtg gtgaaaccga gtgaggtggc gccgctcaac     540
gcctggatgc tcgccgagat catcgatgcg gcaggggttc ccgcaggcgt gttcaatctg     600
gtcagcggca cggaccggt cgtcggtgag gccctcgcct cccaccacga ggtggatatg      660
atctccttca ccgggtcgac caacgccggc aagagagtga gcgaactcgc cgcgcagacc     720
gtcaaacgtg tcgccctcga actcggcggc aagagcgcca acatcgtcct ggacgacgcc     780
gacatcgacg agctcatgcc gaacgcgtg cagtgggcga tgatcaattc cggtcagacc      840
tgctcggctc tgacgcgcct actcgtaccc cgcgcgatac tcaccgaggc ggagacggcg     900
```

```
gcgaagacca tcgcggaggc ctacacggtc ggcgcaccgg acgacccgga caccacgctg    960
ggaccattgg tgtcggcgac ccagctcaaa cgggtgcgcg gctacatcga ccgaggtgtc   1020
caggagggcg ccacgctgat cacaggcggg agcgaacccg tcgagggact ggcggtgggc   1080
tactacgtga agccgacgat attttcggag gtgaccccg acatgacgat tcatcgcgag    1140
gagatcttcg gaccggtgct gtcgatcgcg ccgtacgaca ccgaggagga cgcggtccgc   1200
atcgccaacg acagcgagta cggcttgagg ggcggcgtct ggtccaggga tgtggaccgg   1260
gcacgcgctg tcgccgcccg catgcggacc ggacaggtga tgatcaacgg tggcgaattc   1320
aacccgaacg caccgttcgg tggatacaag cagtcgggca ccggccggga attcgggacc   1380
catgggctcg aagaattcct ggaaatcaag tcgctccagt tctga                   1425
```

<210> SEQ ID NO 12
<211> LENGTH: 474
<212> TYPE: PRT
<213> ORGANISM: Rhodococcus ruber

<400> SEQUENCE: 12

```
Met Thr Ala Gly His Phe Thr Glu Leu Tyr Ile Asn Gly Ser Trp Val
 1               5                  10                  15

Ala Ser Thr Ser Lys Thr Val Ile Glu Val Leu Asn Pro Ala Thr Glu
                20                  25                  30

Glu Val Ile Gly Thr Val Pro Asp Gly Thr Ala Ala Asp Val Asp Ala
            35                  40                  45

Ala Val Ala Ala Ala Arg Ala Ala Phe Asp Gly Trp Ala Ser Thr Pro
        50                  55                  60

Val Asp Lys Arg Ala Gln Tyr Leu Arg Ala Ile Ala Ala Gly Ile Ala
 65                  70                  75                  80

Asp Arg Ser Asp Glu Leu Ala Arg Thr Ile Ser Ala Glu Met Gly Ala
                85                  90                  95

Pro Leu Ser Phe Ala Gln Ala Met Gln Val Pro Leu Pro Ile Asn Ser
            100                 105                 110

Phe Ser His Ala Ala Ala Val Ala Glu Ser Phe Pro Phe Glu Arg Thr
        115                 120                 125

Glu Gly Ser Ser Val Ile Val Arg Glu Pro Ile Gly Val Val Gly Ala
    130                 135                 140

Ile Thr Pro Trp Asn Tyr Pro Leu His Gln Ile Ala Ala Lys Val Ala
145                 150                 155                 160

Tyr Ala Leu Ala Ala Gly Asn Thr Ile Val Val Lys Pro Ser Glu Val
                165                 170                 175

Ala Pro Leu Asn Ala Trp Met Leu Ala Glu Ile Ile Asp Ala Ala Gly
            180                 185                 190

Val Pro Ala Gly Val Phe Asn Leu Val Ser Gly Thr Gly Pro Val Val
        195                 200                 205

Gly Glu Ala Leu Ala Ser His His Glu Val Asp Met Ile Ser Phe Thr
    210                 215                 220

Gly Ser Thr Asn Ala Gly Lys Arg Val Ser Glu Leu Ala Ala Gln Thr
225                 230                 235                 240

Val Lys Arg Val Ala Leu Glu Leu Gly Gly Lys Ser Ala Asn Ile Val
                245                 250                 255

Leu Asp Asp Ala Asp Ile Asp Glu Leu Met Pro Asn Ala Val Gln Trp
            260                 265                 270

Ala Met Ile Asn Ser Gly Gln Thr Cys Ser Ala Leu Thr Arg Leu Leu
        275                 280                 285
```

-continued

Val Pro Arg Ala Ile Leu Thr Glu Ala Glu Thr Ala Ala Lys Thr Ile
    290                 295                 300

Ala Glu Ala Tyr Thr Val Gly Ala Pro Asp Asp Pro Asp Thr Thr Leu
305                 310                 315                 320

Gly Pro Leu Val Ser Ala Thr Gln Leu Lys Arg Val Arg Gly Tyr Ile
                325                 330                 335

Asp Arg Gly Val Gln Glu Gly Ala Thr Leu Ile Thr Gly Gly Ser Glu
            340                 345                 350

Pro Val Glu Gly Leu Ala Val Gly Tyr Tyr Val Lys Pro Thr Ile Phe
        355                 360                 365

Ser Glu Val Thr Pro Asp Met Thr Ile His Arg Glu Glu Ile Phe Gly
    370                 375                 380

Pro Val Leu Ser Ile Ala Pro Tyr Asp Thr Glu Glu Asp Ala Val Arg
385                 390                 395                 400

Ile Ala Asn Asp Ser Glu Tyr Gly Leu Arg Gly Gly Val Trp Ser Arg
                405                 410                 415

Asp Val Asp Arg Ala Arg Ala Val Ala Ala Arg Met Arg Thr Gly Gln
            420                 425                 430

Val Met Ile Asn Gly Gly Glu Phe Asn Pro Asn Ala Pro Phe Gly Gly
        435                 440                 445

Tyr Lys Gln Ser Gly Thr Gly Arg Glu Phe Gly Thr His Gly Leu Glu
    450                 455                 460

Glu Phe Leu Glu Ile Lys Ser Leu Gln Phe
465                 470

<210> SEQ ID NO 13
<211> LENGTH: 10480
<212> TYPE: DNA
<213> ORGANISM: Rhodococcus ruber

<400> SEQUENCE: 13
gactcgttca ccccggctgc cgcggcgatg tcccgggtcc gggcaccggc gaggccggtg      60
cgctgaaaga cctgacgagc cgcctcgatg atccgcaccc gacgttcgtc cgcggtcaat     120
cgcgtttgcg tccccgcggg cgccggcgcc gctgcgcgcc ggcgagcttc actcatcgcg     180
acgcgacaac ggtagtaagc aagtactcca tagcccaaga ctagcggaac cgagacgcac     240
ccccgggccc ggaagcgatg gcacgcacgg cccggaacac cctccggggg ctggcggtgc     300
cccgctcgga gggaagggcc cgccggcggc tcgtgtcgta cggaccggcg ccgagaggcg     360
acgccgcggc cggtccccga cgcgccgagg cggaagcaca ccgagaggtg acctccagcg     420
cctttccctg tgaccttga cacccggt attaaagtaa atacttactt acaccgcctt     480
cgcccggaag aagcggcgcc gcagaaaccg cgactccctg atctcggtcg ccgaaagacg     540
tgacagcgca gcgctgcgcg tgacgagcca ggcggcgaga accaccactg tgaaaggtcc     600
cctgatgacg acgagcatcg accgtgaagc gctccggagg aagtatgcgg aagagcgcga     660
caagcggatc cgaccggacg gaaacgacca gtacattcgc ctcgatcacg tggacggctg     720
gtcgcatgac ccgtacatgc cgatcacgcc ccgcgaaccc aagctcgacc atgtgacgtt     780
cgcattcatc ggcggcggct ctcccggcct ggtcaccgcc gcacgccttc gagaatccgg     840
agtcgagagc gtccgcatca tcgacaaggc cggcgacttc ggtggcgtct ggtactggaa     900
cagatacccc ggcgcgatgt gtgacaccgc agccatggtg tacatgccgc tgctcgagga     960
aaccggctac atgccaccg agaagtacgc gcacggcccc gagatcctcg aacactgcca    1020
acgaatcggc aaacactacg acttgtacga cgacgcgctg ttccacaccg aagtcaccga    1080

```
cctggtctgg caggagcacg atcagcgctg gcggatctcg acgaaccgag gtgaccactt   1140
cacggcccaa ttcgtgggta tgggcaccgg ccctctgcac gtggcgcagc tgccgggcat   1200
ccccgggatc gaatcgttcc gcggcaagtc gttccacacc agtcgatggg actacgacta   1260
caccggcggc gacgcgctgg gcgcgccgat ggacaagctc gcggacaagc gcgtagcggt   1320
gatcggaacc ggcgcgaccg cggtgcagtg cgtgcccgaa ctggccaagt actgcaggga   1380
actgtacgtc gtccaacgca cgccgtcggc ggtcgacgaa cggggaaacc acccgatcga   1440
cgagaagtgg ttcgcgcaga tcgcgacacc cggttggcag aagcgctggc tggacagttt   1500
caccgccatc tgggacggcg tgctcaccga cccgagcgag ttggcgatcg aacacgagga   1560
cctcgtccag gacgggtgga ccgcgctcgg ccagaggatg cgtgcagccg tcggatccgt   1620
gccgatcgag cagtactcgc cggaaaatgt gcagcgggca ctcgaggagg ccgacgacga   1680
gcagatggac cgcatccgcg cccgcgtcga cgagatcgtc accgatcccg ccactgccgc   1740
acagctcaag gcctggttcc gtcagatgtg caagcgaccg tgcttccatg acgactacct   1800
gccggcgttc aatcgcccca acacacatct cgtcgacacg gcggcaaag gggtggagcg   1860 catcaccgag aacggcgtgg tcgttgccgg ggtggagtac gaggtggact gcatcgtcta   1920
cgcctccggg ttcgaattcc tcggcaccgg ctacaccgac cgtgccggat tcgacccgac   1980
gggacgcgac ggggtcaagc tgtcggagca ttgggcgcag ggcacacgaa ccctccacgg   2040
catgcacacc tacgattcc ccaacctgtt cgtgctccag ttgatgcagg cgcagctct   2100 cggatcgaac attccccaca acttcgtcga agccgctcgc gtcgtcgctg cgatagtcga   2160
tcacgtgctg agcaccggca catccagcgt cgagacgacg aaggaggcca agcaggcgtg   2220
ggtgcagctt ctcctcgacc acggccgccc cctcggtaat cccgaatgca ctcccgggcta   2280 ctacaacaac gaaggcaaac ccgccgaact gaaggatcgg ctcaacgtcg gctatccggc   2340
aggctcggca gcgttcttcc gcatgatgga ccactggctt gcggccggca gcttcgacgg   2400
cctcaccttc cgctgagcgc cccggccacg acacgccgga tcccgtcgac ccgacgggat   2460
ccggcgcccc cacccaccca gatctcgagg acaccactat ggatgaaccg accatcggcg   2520
gattctgcga cgaccgattc gccgccgtgc gccacatttt cgagcagaac gtcacgtccg   2580
gggaagaact cggcgccgcc ctcgtcatcg acatcgacgg agagacacgc gtcgacatct   2640
ggggaggatt ccgcgaccag gcccggtcca cgccgtggac cgaggacacc atcgtcaacg   2700
tgtggtcgag cacgaagtcg gtactggcat tggcggcact gatgctcgtc gacgccggcg   2760
agctgaacct cgacgcaccc gtcacgcgct actggcccga gttcgccgcc aacggcaaga   2820
gcgacatcgc ggtacggcac atcctctcgc cacctccgg ggtgtcgggc tgggaacagc   2880
ccttcgtcct cgaggacatg tacgactggg acaagtcgac gaccctgctc gcgcagcaag   2940
caccatggtg gccggcgggt tcggccgccg gctaccacgc caacaaccag gccaccctca   3000
tcggagaaat cgtccgccgc atcaccggcc gaccgttcaa ggagttcgtc accacacaca   3060
tcgccggtcc gctcgctgcc gacttccaga tcggcgcccg cgagaacgat tggggccgta   3120
ccgccgagat cgtcgcacca ccccccttcg acatcgatct cgccgcactc gatcccgaca   3180
gcgtcatggt gaagacgatg acgggaccgg tagccgacgc gaacgcggcc aatactcccg   3240
gatggcggca cgccgacatg ggagccctca acggtcacgg caacgcacgc tcgctcgctc   3300
ggatcctctc gaccatcacg ctgggcggtg agagcaacgg cctccgcctc ctccacagca   3360
cctcgatcgg caagattttc gaagagcaga acaacgacgt cgacctcgtc ctcggtgtgc   3420
cgttccgccg cggcatcggc tacgcgctac cgcgccccga caccacgccg agcatcccgg   3480
```

```
agggccggat ctgcttctgg ggtggatggg gtggatcgat gacagtgatg gacctcgacc   3540
gccggatgac gttcacctac gtgatgaaca agatgggggcc aggcatcatc ggatcggccc   3600
ggagcgagca gtacctgcgc gccacctacg atgccctcag cgagacggtc accgcgtgac   3660
acgccgacac cgaaaacccg aaacgagggc cacgcacggc gtgcacgctc gatccagggt   3720
gcactctcct acggcccgcg gctgatgctc gaactgaccg atggtcaacc gatactccca   3780
cggtccccct cggtaccaca tgtcgtcatg gctgtttcgg gccagacgga ggttgctgca   3840
cggtggtgag acggacggat agagcgcttc ccagaagcat gattccttcg aagcgactgg   3900
ggtcgatccc cgtcaggctt gcgatgcggt ggagcctgtt gttcaccgtg ttggggtgca   3960
cctggagacg tcgcgccgtg cgtcctcggt cgaagtcgag gaacaagtag tggtccagtg   4020
tctcgagtag ttcagggtac ggctcgaggg ggacgaggag atcgaagaga taacgggtgg   4080
ctgcggtcgg tcgggacagc tggtaggcaa gagtcacatc tgccagtcgg tagaggccgg   4140
ggggacggtt tgtagagatg acgatctcca ggatctcgct ggacaatttt gcggcgcggg   4200
gcaggtcgtc gaagctggca gagtctacgt gactggccgt gaccttcact tccgcggcga   4260
cccgcatgcg gtctatgaga tcgcgcccca cttcgtccgt cgtcgctgtc gcggtctcgt   4320
cgtggggaac gagaacgtgc ccaccatggg gatcgagggt ggccagcacc gggtgggcac   4380
cgcggtactc gcccagagtg cgcaggattt tccgcagttt tcggcggttc gcgatctgat   4440
gaccgggatg tggtccgacg ggttcctggt cgaacggagt gaacttgaca gccatcacgt   4500
catagcgcgg cgcgagttcg accccgagct gctcggcctc ggcgtgagcg ctgcgaccgc   4560
tgagaagcgt tcttgccacg aggtacacgg cgccacgctc accgttggcg atggcttcgc   4620
gctctgcctg gtaggacgtg gtgaccgtac tgaggatctc ctgctgcagg gtcagcagct   4680
tgcgcccgat ataaccgagt gcgtgcgcgt cgtcgtcttg gccgcgtcc  gtgcaggcat   4740
tccacaagac ggtcatgccg ttttgccagt tgcgcaacac caaggcgagg ggaacccctt   4800
cgatcgctct gtctgcggcg atctcttgca ccattcgtaa gtcacgttct tcgaacggcg   4860
cattgttccg gatgagctga atgtagaggc gaaagtaccg ccgcttcaat tgcggaatttt  4920
cctgctgccg gaaatcgatc ggcagattct ggtattcctg ttggccgtcc gcttcgctcg   4980
gctcggcgag tacgtgaatc cgggattgca cggtgtcgag cacgcgccgc actgcgggt    5040
ccgcccccga accctccccc atcacttcgc gaacctcctc gttaccgaga ctgtgctgtc   5100
gcacaatatc agagggggctt gactatggaa aagagctatt gagctggtca caggcacatc   5160
atagcctttc ctcaacaggc aatcgtgttc cgcatcacac tcaagcgcgc tgggtcgatg   5220
agggtccgca gttgccagcc gacctggtcg acgtcgggcc cggggcagca cgcaaggctg   5280
cccgactcga tcactcatct cgcaatcaat cgaacgtgga aacggtgaag gaatctcatc   5340
atgactgtta agggaaagtc ggcgacagcg acgaccaagg ctgcgaaccg cgccgtgtct   5400
gctcgcctgg acttcgacga caagacggcg ttcgacgatg cgcgccgtgg cttcgtcgcc   5460
acactcgatc cgctggtgat cagaaacgct caaggtcatg tcgtgtggga cggcgatacc   5520
tacgccttcc tcgccgacga ggcaccggac acggtgaacc cgagcctgtg gcgcatgtcg   5580
caactacata cgattcacgg cctgttcaag gtcgtcgacg gcatctatca ggtgcgcggc   5640
ttcgacatct ccaacatgac tctggtcgag ggcgacaccg gatacgtcgt catcgatccg   5700
ctgacctcgg ccgaatgcgc ttcggcggcc atggatctgg tgcgcaggga actcggtgac   5760
cggccggtga cggcgatcgt ctacacccac agccacgtcg atcatttcgg tggtgtgaaa   5820
gggctcgtgt cggaggcgga catctccgcg ggttccgtgc ggatcgtcgc gccgacgggg   5880
```

-continued

| | |
|---|---|
| ttcctggccc acacggtcag cgagaacgtc tacgccggca acgcgatgaa ccgccgtgcg | 5940 |
| cagtacatgc acggcggcaa gctgccgcac gggccgagcg gggtggtctc ggccggtctc | 6000 |
| ggcctcgggc tctccaccgg caccgtcacg ctgctcgagc ccaccgatta cgtcaccgag | 6060 |
| accggtcagg aactcgtgct cgacggggtg cggttcgagt ttcagtacac gcccgacgcc | 6120 |
| gaggcaccgg ccgagatgaa cttctacctg cccgatttcc gggcgctgtg catggcggag | 6180 |
| aacgtctctc accacatgca caacctgtac accccccgcg gcgcgcagat tcgtgacgct | 6240 |
| gccgcgtgga gcgactacat ccatgccgcg atcgggctct atgcgcaccg gtcggacgtg | 6300 |
| ctgttcatct gtcaccactg gccggtgtgg ggtcggcaga agctcaccga cttcttggag | 6360 |
| cagcagcggg acctgtaccg ctacatccac gacgagaccc tgcgtctggc cgcccacggc | 6420 |
| cacacgctgg tcgagatcgc cgaactgatc gagctgcccg agccgctggg ctcgtcgtgg | 6480 |
| tcgagccgcg gctactacgg caccttgaac acaacgcca aggcggtcta tcagaagtac | 6540 |
| ctcggctggt tcgacggcaa tccggccacc ttgcaccagc atccaccggt cgaggcgggt | 6600 |
| aagcgctacg tcgaatacat gggcggagcc gacgccgtgc tgcgcaatgc gcgcaaatcg | 6660 |
| ttcgacgacg gggactaccg gtgggtggcc caggtggtca accatgtggt gttcgccgag | 6720 |
| ccggacaacc agcaggcacg ggaactgcag gcggacgcgc tcgaacagct cggctaccag | 6780 |
| gccgaatccg cttcgtggcg caacttctat ctcaccggtg cccaggaact gcgtcacggt | 6840 |
| gtggtggtgg agtcgacctc gttcgacacc tcggacgtgc tggccgcgat gacgacggac | 6900 |
| atgatgctca agtatctggc catccgtctg aacggaccga aggccgccgg ccgtgccttg | 6960 |
| cgggtcgacc tgcacgtgac cgacaccgac gagcgccggc tgctgcaggt gaccaacggt | 7020 |
| gtcctcgtcc acacggcgac gagcgcgccc caggatgcgc acgtgtcggt cgcgctcacc | 7080 |
| cgggccgcgc tcggatcgct gacgctcggc ggcacggccc tcgaccggtg cattgccgac | 7140 |
| ggcagcgtct cggtcggcgg caatgccgac gtgcttcgcg aactgttcgc gctgctcgac | 7200 |
| actttcgacc ggttcttcga catcgtcacc ccctgaacct tcccccgggg ccgcggcgaa | 7260 |
| gcacccccct tgcaatccac gacaggagca gaacatgaag acgaaggcag ccgtcctccg | 7320 |
| cggagtcggt caggactggc ggatcgagga gatcgagctc ggcgatccgg tccccggcga | 7380 |
| ggtccaggtc cgactcgtgg cgtcggggat gtgccactcc gatcaccacc tgcggaccgg | 7440 |
| tggtagcccg attccgtttc ccgtgatcgg cggtcacgag gggtcgggca tcgtcaccaa | 7500 |
| ggtcggcccc ggtgtcacct ctctcgtcga gggcgatcat gtggtgacgg cgttcatccc | 7560 |
| ggcgtgcgga acctgcgggc cgtgctcgcg gggtctgcag aatctgtgtg acgagggtgc | 7620 |
| ggggctgctc accggtaggt ccatctccga cgggacctac cgggcgagcg cgaagggcga | 7680 |
| accactggtg ccgatgtgcc tgctcggcac gttctctccg tacatcaccg tcaacgaggc | 7740 |
| gtcgttggtg aagatcgaga aggacattcc cctcgaagct cgcgcgctgc tcggctgcgg | 7800 |
| ggtggctacc gggtgggtt cggcgaccgc gatcggcggc accaaggtcg gtgacaccgt | 7860 |
| ggtggtcgtc ggcgtcggag gtgtgggcat caatgccgtc cagggcgcgg ctgccgccgg | 7920 |
| ggcgcgccac gtcatcgccg tcgacccggt ggagttcaag cgacacatgg ccctcgcact | 7980 |
| cggtgcgacg cacgtgtatg cctccctcga agaggcgatg gaaccggtcc gggacctgac | 8040 |
| ctggggcctg atggcggacg tgacggtctt gaccgtgggc gacatcgaag cgacatcat | 8100 |
| ccagccggcg ctgaccatca cggccaaggc cggccaggtc gtcgtcaccg ctatgggtga | 8160 |
| cgcgacaaag aacgaggtga cactcaacct cttcgagctg acgctgctgc agaagcgggt | 8220 |
| ccagggcgcc atcttcggcg gtgtggggc gcgcacccag atccccgctc tcctgcatca | 8280 |

```
ctatcgcagc ggtgcgctca agctcgagga actcgccacc accgtctatc gcctcgagga      8340
cgtcaaccag ggctacgacg acatgttggc gggcaagaac ctgcgcggca tcatccggta      8400
caccgacgcc gacttctgat cccaatcccc ctcccccaag ccacagacgg agtacgacat      8460
gaccgctggc catttcaccg agctctacat caacggttcc tgggttgcct cgacaagcaa      8520
gacggtgatc gaggtgctca accccgcaac cgaagaggtg atcgggactg tcccggacgg      8580
gaccgcagca gatgtggacg cggcggtggc cgctgcccgg ccgcgttcg acggctgggc       8640 gagcacaccg gtcgacaagc gcgcgcagta cctacgggcc atcgccgccg gcatcgccga      8700
ccgcagcgac gagctggcac gcaccatctc tgccgagatg ggcgctccgc tgtcgtttgc      8760
ccaggccatg caggtgcccc tgccgatcaa cagcttctcg catgcagcgg ccgtggcgga      8820
gagcttcccg ttcgaacgca ccgagggctc atcggtgatc gtgcgggaac cgatcggggt      8880
ggtgggggcg atcaccccgt ggaactatcc cctgcaccag atcgccgcga aggtcgccta      8940
cgccctcgcc gccggcaaca ccatcgtggt gaaaccgagt gaggtggcgc cgctcaacgc      9000
ctggatgctc gccgagatca tcgatgcggc aggggttccc gcaggcgtgt tcaatctggt      9060
cagcggcacg ggaccggtcg tcggtgaggc cctcgcctcc caccacgagg tggatatgat      9120
ctccttcacc gggtcgacca acgccggcaa gagagtgagc gaactcgccg cgcagaccgt      9180
caaacgtgtc gccctcgaac tcggcggcaa gagcgccaac atcgtcctgg acgacgccga      9240
catcgacgag ctcatgccga acgcggtgca gtgggcgatg atcaattccg gtcagacctg      9300
ctcggctctg acgcgcctac tcgtaccccg cgcgatactc accgaggcgg agacggcggc      9360
gaagaccatc gcggaggcct acacggtcgg cgcaccggac gacccggaca ccacgctggg      9420
accattggtg tcgcgacccc agctcaaacg ggtgcgcggc tacatcgacc gaggtgtcca      9480
ggagggcgcc acgctgatca caggcgggag cgaacccgtc gagggactgg cggtgggcta      9540
ctacgtgaag ccgacgatat tttcggaggt gaccccgac atgacgattc atcgcgagga       9600
gatcttcgga ccggtgctgt cgatcgcgcc gtacgacacc gaggaggacg cggtccgcat      9660
cgccaacgac agcgagtacg gcttgagggg cggcgtctgg tccagggatg tggacgggc       9720 acgcgctgtc gccgcccgca tgcggaccgg acaggtgatg atcaacggtg gcgaattcaa      9780
cccgaacgca ccgttcggtg gatacaagca gtcgggcacc ggccgggaat cggggaccca     9840
tgggctcgaa gaattcctgg aaatcaagtc gctccagttc tgacctcgct cacatgtagg      9900
gggatcggtc gtaccagggc agatccccct gcgtgctctg cggcgcacat ctcagccagc      9960 accccagaa agaaccccgc gatgaacctt ccccttgacc ctcgtgttcg tcgggctcgg      10020
cagcagtcgg tgtcggacct gctgcatcgg acggccgccc ggtaccccgc caagaccgct     10080
gtgatcgacg gcaacacctc gttcgacttt gccgaattcg acagcgtcgt cagctccctc     10140
gcggcccact tgcagcgcag cggtcttgag aagggtgatc ggctcgcttt gctgcccgc       10200 aactcgtggc aattcgcggc gttgtctttt gcgaccgcgc ggatcggtgt ccttctcgtc     10260
ccgatcaact tcatgctcaa atccgaggaa gtggcgttca tcctcgagca ctccggttcg     10320
cgagccgtcg ccgcggacgc cgagtttcgt cccggtcctt gcaggacgcc atccgcatcg     10380
ccggcacgga cgtcgtgctt ccgcggctgg atcggccgaa gtgatccggc ccctgggtgg     10440
ggaaagtgtg gagacgtgga cgaaacacgc ccgccgatct                           10480

<210> SEQ ID NO 14
<211> LENGTH: 20
<212> TYPE: PRT
<213> ORGANISM: Rhodococcus ruber
```

```
<220> FEATURE:
<223> OTHER INFORMATION: N-Terminal Amino Acid Sequence

<400> SEQUENCE: 14

Thr Thr Ser Ile Asp Arg Glu Ala Leu Arg Arg Lys Tyr Ala Glu Glu
 1               5                  10                  15

Arg Asp Lys Arg
          20

<210> SEQ ID NO 15
<211> LENGTH: 11
<212> TYPE: PRT
<213> ORGANISM: Rhodococcus ruber
<220> FEATURE:
<223> OTHER INFORMATION: Internal Peptide Amino Acid Sequence

<400> SEQUENCE: 15

Glu Arg Ile Arg Ala Arg Val Asp Glu Ile Gly
 1               5                  10

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: JCR14
      Primer

<400> SEQUENCE: 16
acgggcggtg tgtac                                                        15

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence:JCR15 Primer

<400> SEQUENCE: 17
gccagcagcc gcggta                                                       16

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:cddk4 primer
<221> NAME/KEY: unsure
<222> LOCATION: (3)
<223> OTHER INFORMATION: R=A OR G
<221> NAME/KEY: unsure
<222> LOCATION: (6)
<223> OTHER INFORMATION: Y=C or T
<221> NAME/KEY: unsure
<222> LOCATION: (9)
<223> OTHER INFORMATION: N=A or C or G or T
<221> NAME/KEY: unsure
<222> LOCATION: (12)
<223> OTHER INFORMATION: R=A or G
<221> NAME/KEY: unsure
<222> LOCATION: (15)
<223> OTHER INFORMATION: R=A or G
<221> NAME/KEY: unsure
<222> LOCATION: (21)
<223> OTHER INFORMATION: Y=C or T
<221> NAME/KEY: unsure
<222> LOCATION: (18)
<223> OTHER INFORMATION: N=A or C or G or T
```

```
<400> SEQUENCE: 18
aartaygcng argarcgnga yaa                                        23

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:cddk10
      primer
<221> NAME/KEY: unsure
<222> LOCATION: (3)
<223> OTHER INFORMATION: D=A or G or T,
<221> NAME/KEY: unsure
<222> LOCATION: (6)
<223> OTHER INFORMATION: Y=C or T,
<221> NAME/KEY: unsure
<222> LOCATION: (9)
<223> OTHER INFORMATION: R=A or G
<221> NAME/KEY: unsure
<222> LOCATION: (10)
<223> OTHER INFORMATION: R=A or G
<221> NAME/KEY: unsure
<222> LOCATION: (12)
<223> OTHER INFORMATION: N=A or C or G or T
<221> NAME/KEY: unsure
<222> LOCATION: (15)
<223> OTHER INFORMATION: N=A or C or G or T
<221> NAME/KEY: unsure
<222> LOCATION: (18)
<223> OTHER INFORMATION: N=A or C or G or T

<400> SEQUENCE: 19
ccdatytcrr cnacnckngc                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:C12 MO TOP
      Primer

<400> SEQUENCE: 20
atgcagagga gcgggacaag                                            20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:C12 MO
      BOTTOM Primer

<400> SEQUENCE: 21
acttcggtgt ggaacagcgc                                            20

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:KK1 Primer

<400> SEQUENCE: 22
ccccaagctt gaacccagcc cctgcaagat                                 30

<210> SEQ ID NO 23
<211> LENGTH: 30
```

```
<212> TYPE: DNA
<213> ORGANISM: Artificial Sequence
<220> FEATURE:
<223> OTHER INFORMATION: Description of Artificial Sequence: KK2 Primer

<400> SEQUENCE: 23
ggactagttc agttcgagca tcagccgcgg                                        30

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence:KK3 Primer

<400> SEQUENCE: 24
ggactagtga acccagcccc tgcaagat                                          28

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:KK4 Primer

<400> SEQUENCE: 25
ccccaagctt gtaggagagt gcaccctgga                                        30

<210> SEQ ID NO 26
<211> LENGTH: 1812
<212> TYPE: DNA
<213> ORGANISM: Artificial Sequence
<220> FEATURE:
<223> OTHER INFORMATION: Description of Artificial Sequence:CddA homolog

<400> SEQUENCE: 26
atgacgacga gcaacggccg tgaagcgctc cggacgaagc aagcggaaga gcgcgacatg        60
cggatccgac cggacggaaa ggtccagtac attagcctcg atctcgtgta cgtctggtcg       120
catgactcgt acatgctgct cacgccccgc aaacccaaga tggaccatgt gacgttcgca       180
tacatcggcg gcggcgtctc cggcgtggtg tgcgacgcac acctgcgaga ctccggagtc       240
gagggcgtcg gcatcatcta caaggccggc tatttcggag gcgtctggtg ctggaaccga       300
taccccggcg cgatgtgtgc caccgcagcc atggcgcaca tgccgcggct tgaggaaacc       360
ggctacctac ccaacggcaa ctacgcgcac ggcccggaga tcctcgaata ctgccaacga       420
atcggcaaac accacgactt ctacgacgac gcgctgttca acatcgaagt ctccaacatg       480
gtctcgcagg aacagggcca gcactggcgg accccgacgg acccaggggg ccacttcacg       540
gcccaaatca ggggtatggg caccggccct ctgcacgtgg cgcaggtgcc cgtcatcccc       600
gggatccgat cgttccgcag ggagacgttc cacaccagtc gatggggcca acacgagacc       660
ggcggcgacg cgatggtcgc gccgatggac aagctggcgg acaagcacgt agcggtaatc       720
ggaaccggcg cgaccgccgt gcagtgggtg cccgaacttg ccaagtactg cagggaactg       780
caagtagtcg aacggacgcc gtcgacggtc gacgaacgga gaaccacccc gaccgacgag       840
aagcggttcg cgcagatcgc gacgccaggt tggcagaagc gctgtatgga cagttttcacc      900 gccatctggg agtgtgtgct caccgaccgg agcgagttgg cgatccaaca cgagtacctc       960
gtccaggacg ggagaaccgc gctcggcaag agtaagcgtg cagcagtcgg acccgtgccc      1020
atcgagcagt actcgctgga aaaagggcag cgtgcgctcg aggatgacgg cgacgagcag      1080
```

```
atggagcgca tccgtgcccg cgtcgacgac attgtcacca atcccgccag ggccgcacag    1140
ctcaaggcgt cgttacgtca gttgtgcaag agaacgtgct tccatgacga ccacctgccg    1200
gcgttcaatg ggcgcaacac acttctcgtc gacacggggg ccaaaggtgt ggagcgcatc    1260
accgaaaacg gcatagtcgt tgacgggctg gagtaccagg tggactgcat cgtccaagcc    1320
tccgggttcg aagtcctccg caccgactac accgatcgtg ccggattcga cccgccggga    1380
cgcgacgggg tcaagttgtc ggagcattgg gcgcaggaca cacgaaccct ccacggcatg    1440
aacacctacg gattccccaa cctgttcgtg ctgcaggtga ggcagcgcgc acctctcgga    1500
tcgaacattc cccacaactt cgtcgaagcc tctcgcgtcg ttgctgagat agtcgatcac    1560
gtgctgcgga ccggcacatc caacgacgag acgacgaagg aggcggagca ggcttgggtg    1620
caggttctcc ccgaccaggg ccggcgcctc gctaatcccg aaagagctcc gggcaacatc    1680
aacaacgaag gcagacccgc cgaagtgaac catcggccca acgtcggcta tcggggaggc    1740
tcggcagcgt tcttcccaat tatcgaccat tggcttgcag ccggcagctt gaacggcctc    1800
accttctgct ga                                                        1812

<210> SEQ ID NO 27
<211> LENGTH: 1812
<212> TYPE: DNA
<213> ORGANISM: Artificial Sequence
<220> FEATURE:
<223> OTHER INFORMATION: Description of Artificial Sequence:CddA Homolog

<400> SEQUENCE: 27
atgacgaaga gcatcgtccg cgaggcgctc cggcggaagt acgcggaaga gcgcgacaag      60
cggatccgcc cagacggaag cgagcagtac attcgcctcg atcacgtgga cggctggtcg     120
catgacccgt acatgccgat cacgctccgc aaacccaagc tcgaccattt gatgttcgca     180
ttcatcggcg gcggatgctc cggctggtc accgccgaaa cccttcgaga atccggagtg      240
gagggcgtcc gcctcatcca caaggccggc gacttcggtg acgtctggta ctggtacaga     300
taccccggcg cgacgtgtga aaccggagcc atggtgttca tgccgctgct cgaggaaacc     360
ggctgcatgc ccgccgagaa gtacgcgcac cgcccggacg acctcgaaca ctgccaacgc     420
atcggcaaac actacgtctt gtgcgacgac acgccgttcc acaccgacgt caccgacctg     480
gtctgggagc agcacgaaca gcgctggcgg atctcgatga accgagctga ccacttcacg     540
cccctattcg tgggtatggg caccagcccg ctgcacgtgg cgcacctgcc gggcatcccc     600
gggatcgaat cgatccgcgg caactcgttc ctgactagtc gaagagacta cgactacacc     660
ggaggcgacg cgctgggcgc gcctatggac gagctcgagg acaagcgcgt agcggtgatc     720
ggaaccggag cgaccgcagt gcagtgtgta cacaaactgg cgaagtactg cagggaactg     780
tacatcgtcc aacgcacgcc gtcggcgtgc gacgatcgag gaaagcaccc gatcgacgag     840
aagtggttcg cgcagatcgc gactcctgga agacagaagc gctggcagga cagtttcccc     900
gccagctggg acgcgtgct caccgacccg tgcgagttgg cgatcgaaca cgaggacctc      960
gtcgaggacg ggtggaccgc gctcgtccag cggatgcgtg cagccctcgg atcagtgccg    1020
atcgagcagt actcgccgga aaatctgcag agggcaatcg aggaggccaa ggacgaggag    1080
gttgagcaca tccgcgcccg cgtcgacgag ctcgtaaccg atcccgctac tgccgtacag    1140
ctcaaggcct ggttccgtca aatgtacaat cgaccgtgct tccatgacga ctacctgccg    1200
gcgttcaaac ggccgaacac acatcccgcc gacacgagcg gcaaagggt ggaacgtatc     1260 accgagaacg gctgggtcgt tgccggtgtg gagtacgagg tggactgcat cgtctacgcc    1320
```

-continued

```
gccgggttcg tgttcctcgg caccggctac accgaccgtg ccggattcga cccgacggga      1380
cgcgacgtgg tcaagcggtc ggagccttgg gcgcagggca cgaaccttt ccacggcatg       1440 cacacctacg gattccccaa ccttttcgtg ctccatttga atgagggagc agctctcgga      1500
ccgaacatcc cccacaactt cgtcgaagcc gctcgcattg tcgcttcgat agtcgatcac      1560
gtgcggagca ccggcacatc cagcgtcgag acgacgaagg aggccgagca ggcgtgggtg      1620
cagcttctcc tagaccacgg ccggcccctc ggtaatctcg aatgcgttcc gagcaactac      1680
aacaacgacg gcaaacccgc ggaagcgaag gatcgggtca acctcggcta tccgttaggc      1740
tctgcagagt tcttccgcat gctggaccat tggcttgcgg ccggcagctt cgacggcctc      1800
accttccgct ga                                                          1812
```

<210> SEQ ID NO 28
<211> LENGTH: 1812
<212> TYPE: DNA
<213> ORGANISM: Artificial Sequence
<220> FEATURE:
<223> OTHER INFORMATION: Description of Artificial Sequence:CddA Homolog

<400> SEQUENCE: 28

```
atgacgacta gcatcgacct accagcgcgc catatgaagt atgcggaaga gcgaaacaag       60
cggatccggc cggacggaac cgaccagtac attcgcctcg atcacgtaga cggccggacc      120
catgacccgt acatgccgat cacgctccgc gattccaagc tagaccatgt ggcattcgca      180
ttcatcggcg tcggcttctc aggcctggtc acctccgcac cccttcgaga atccggagtc      240
gggagcgccc gcatcatcga caaggccgcc gacatcggtg cgtctggta ctggaacaga       300 taccccggag cgatgtgcga caccgcatcc atggtgtaca tgccgcttct cgaggaaacg      360
gcctacatgc cgacagagaa gtacgcgcac ggcccgggga acctcgaaca ctgccaacga      420
atcggcacac actacgactt gtacgaccac gcgctgttcc acaccgaagt caccgacctg      480
gtctggcagg agcacgatca gcggtggcgg atctcggcga accgaggcga ccacttcacg      540
gctcaattcg tgggtatggg caccggcccc tgcgcgtgg ctcagctgcc gggcatgccc       600
gggagcgaat ccttgcgcgg caagttgttc cacaccaggc aatggcacta cgactacacc      660
ggcggcgacg cgctgggcgc gccgtgggac aagctcgagg acaagcgctt agcggtgatc      720
ggaaccggcg cgaccgcggt tcagtgcctg cccgaactgc ccacgtactg cagggatcgg      780
tacgtagtcc aactcacgcc ttcggctgtc gacgaacgga gaaacctcct gatcgacgag      840
aagtgcgtcg cgcagatcgc gaccgccggt tggcagaagt gctggttgga cagtttcacc      900
gccatcgagt actgcgtgct caccgacccg agcgagttgg cgatcgtaga cgtggacctc      960
gtcgagaagg gttcgaacgc gctcggccag aggatgcgac cagccgtcgg gtccgagccg     1020
atcgcgcagt actcgcccga aaatgtgcag cgggcaatcg aggaggccgc cgacaagcag     1080
atggagcgca tccgcaccgg catcgacgag atcggcaccg atcaggccac tgccgcacag     1140
ctcaaggcct ggttccgtca gatgaacaag cgaccgtgct tccatgacga ctccctgccg     1200
gcgttcaatc agctcaacgc acatctcgtc gacacgcgcg gcaaaggggt ggagcgcatc     1260
aaggagaacg gcgtggtcgt tgccgtgggg gggcacgagg tggactgcat agtccaagcc     1320
tccgggttcg aattcctcgg cacaggctac accgaccta ccggattcga cccgacgaga     1380
cgcgacgggt tgaagctgtc ggagcttggg gggaaaggca cgaaccct ccacggcatg      1440 cacacctacg gattaaccaa cctgttcgtt ctcctgttga ttcaggacgc agctgtcaga     1500
tcgaacagtc cccacaactt cgtcggagcc gcacgcgtcg tcgctccgat agtcgatcac     1560
```

-continued

```
gagttcagcc ccggcacgtc cggcgtccag aagacgaagg aggccgagca ggcgtgggtg    1620
cggcttcttc ccgaccaagg ccagcccctc ggtactcccg aatgcactcc gggctacgac    1680
aacaacgaag cgcaacccgc cccactgaac gatcggcgca acaggggcta tccctcaggc    1740
tcggaagcgt tcttccgtat gatggaccac tggctggcgg cccgcagctt cgaaggcctc    1800
ccctgccgct ga                                                        1812
```

<210> SEQ ID NO 29
<211> LENGTH: 1161
<212> TYPE: DNA
<213> ORGANISM: Artificial Sequence
<220> FEATURE:
<223> OTHER INFORMATION: Description of Artificial Sequence:CddB Homolog

<400> SEQUENCE: 29

```
atggatgaac cgaacaccgg cggattctgc gacggccgat tagccgccgt gcgccacagt     60
ttcgagcaga acgtcacgtc ggtggaagaa ctcagcgccg cccgcgtctt cgtcatcgac    120
ggagagtcac gcgtcgtcct ctggggagga atccgcgaca acgcccggtc cacgccgtgg    180
aacgaggaca ccatcttcaa cgtgcggtcc tccaagaagg aggttctggc cttggcggca    240
ctggtgctcc tcgacgcctg cgagctgaac cttgacgccc ccgtcacgcc ctactggccc    300
gagttcggcg ccaacggcaa gagcgacatc gcggcagggc acatccgctc tcacacctcc    360
ggggtgacag gcgaggggca ccccttcgtc ctcgaggaca tgtacgacgg ggacaagtcg    420
acgaccctgc tcccgcagca ggcaccatgg tggccggcga gtttggccgc ctgcaacaac    480
gccagcaacc aagggcggct caacggagaa accctccgcg gcaccactgc ccgaccgttc    540
aaggagatca gcaccacaca catcgccggt ccgctcgctg ccgacctcca cagcggcgcc    600
cgcgagggcg attggggcag cgccaccgag atcgtcgcac cacccgcctt acacatggat    660
ctcgccgcac tcaatctcga cagcgtcatg gtgaacacga tgacgaacc ggtagcagac    720 gcgaacgcgg ccaatacccc cggatgccgg cacgccgata tgggagccct caacggtcac    780
cgaaaagcag gctccctcgc tcggctcctc tcgaccatcc cgctgggcgg tgggagcaac    840
ggcgtccgcc tcctccacag cacgtcaatc ggcaagattt tcgataagca gaacaacgac    900
gtcgacctcg tgtttggtgt gccgttcccc cgcggcatcg gctacccgct accgtgcccc    960
gacaccacgc cgcgaatccc ggagggcagg atttacttct ggggaggatg gggtggatcg   1020
atgacagtga tggaccgcga ccgactgatg actttgacct acgttaagag caagatgggg   1080
ccaggcatca tcggttcggc ccggagcgac cattacctga gcgccacctg tgatgccctc   1140
agcgagaccg ccacagcgtg a                                             1161
```

<210> SEQ ID NO 30
<211> LENGTH: 1161
<212> TYPE: DNA
<213> ORGANISM: Artificial Sequence
<220> FEATURE:
<223> OTHER INFORMATION: Description of Artificial Sequence:CddB Homolog

<400> SEQUENCE: 30

```
atggatgcac cgaccagcgg ggggttctgc gacaaccgat tggccgccgt gcgccacatt     60
ttcgagcaaa aagtcacgtg cggcgaagaa ctcggcgccg ccctcgtcat cgacatcgac    120
ggagagacac gcgtcgacat ctgggtagga atccgcgacc aggccgggc catgccgtgg    180 accgagggca ccataggcaa cgtctggtcg agcacgacga gggtactggc attggcggcg    240
ctggtgctcg tcaacgcccg cgagctgaac ctcgacgcac ccgtcacgcg ctactggccc    300
```

-continued

```
gagttcgccg ccagcggcaa aagcggcatc gcggtactgc acatcctctc gcacacctcc      360
ggggcgtcgg gccgggaaca gcccttcgtc gtcgaggagg agtacgactg ggacaagtca      420
acgaccctgc tcgcgctgca aggaccatgg aggcgggcgg gttcggcagc cggctaccac      480
gccaactacg agggccaact catcggagaa atcgtcctcc gcatcagcgg ccgaccgttc      540
gaggtgttcg tcaccacaca catcaccggg ccgctcgctg ccgagttcca gatcggcgcc      600
cgcgagaacg ataggggccg tacggccgag agggttgcac caccacccct cgacatcgat      660
ctagccgcac tcgatcccga cagtgtcatg ttgaagaaga tgacgggacc ggtaggcgac      720
gcggacgcag ccaatacacc cggatgtcga cccaccgaca tcggagccct caacggtcac      780
ggccacgcac gctcgctcgc tcggatctgc tcgactataa cgctcggcgg tgagagcaac      840
ggcctccgcc tcctccacag cacttctata ggaaagattt tcgaagcgca gaacaacaac      900
gtcgtcctcg tcctcggtgt gccgttccgc tgcggcatcg gctacgcgct accgcgcccc      960
gactccacgc cgagcatccc ggaggtccgg ctctgcttct ggggtggatg gggaggatcg     1020
atgacagtga tggacctcga ccgcgggatg ccgttccccg acgtgatgca aagatgcgg      1080 gctggcaaca tcggatcggc ccggagcgag aagcaactgc gcgccactta cgatgtcctc      1140
agcgagacgg tcaccgcgtg a                                                1161
```

<210> SEQ ID NO 31
<211> LENGTH: 1161
<212> TYPE: DNA
<213> ORGANISM: Artificial Sequence
<220> FEATURE:
<223> OTHER INFORMATION: Description of Artificial Sequence:CddB Homolog
<400> SEQUENCE: 31

```
atgtatgaac cgaccgtcgg cggattctgc gacgaccgat tcgccgccgt gagccacatt       60
ttcgagcaga acgtcacttc gcgcgaagaa ctcggcgccg ccctcgtcat cgactgcgac      120
ggagagacac gcgtcgacat ctggggagga ttacgcgacc aggcccggtc gacgccgtgg      180
accgagtaca ataccgtgaa cgtgtcttcg agcacgaagt cgatactggc attggcggca      240
ctgatgctcg tcgacgccag cgagctgaac ctcgacgcac ccgtcacgcg ctactggccc      300
gaattcgctg ccaacggcaa gaccgacatc gcggtacggc acatcctctc gcacacctcc      360 gggggtcgg gctctgaaca gcccctcgtc ctcgaggaca tggacatctg gacaagtcg       420 acgacccgc tcgcgtcgca ggcaccatgg agaccagcgg gttcggccgc cggctaccac      480
tcgaacaacc aggggcacct catcagagaa atcttccgcc gcatcgccgg ccgaccgttc      540
agggagttcg tgactacaca catcgccgat ccgctcgcta ccgacttcca gatcggcggc      600
cgcgagaacg attggggccg taccggcgag gtcgtagcac ttcccccctt cgctatcgat      660
atcgctgcac tcgatccgga cagcgtcatg gtgaacacga tgacgggacc ggttgtcgag      720
tcgaacgcag ccaatgctcc cgcttggcga ctcgccgtcg tgggagcctt caacggtcgc      780
ggccatgcac gcacgctcgc tctcatcctc tccaccatca cgctgggcgg tgcgagtaat      840
ggcctccgtc tcctccacgg aatctcgatc gggcagattc tcgaagagca aacaacgac      900 gtcgacgtcc tccccggagt gccgttccgc cgcgacatcg gctacgcgct accgcgcccc      960
gacaccaaga cgagcatcat ggaggtcggg atctgcttgt ggggtggatg gggtggatcg     1020
atgacagtac tggagcccga cgcctgatg acgttcacct acgtgatgaa caagatgggg      1080
ccagtcatca tcgcagcgtt ccggagcgag cagtacctgc ccgccaccta cgatgccctc     1140
agcgagacgg tcaccgcttg a                                                1161
```

<210> SEQ ID NO 32
<211> LENGTH: 1125
<212> TYPE: DNA
<213> ORGANISM: Artificial Sequence
<220> FEATURE:
<223> OTHER INFORMATION: Description of Artificial Sequence:CddC Homolog

<400> SEQUENCE: 32

| | | | | | |
|---|---|---|---|---|---|
| atgaagaaga | aggcagtcgt | gctgcgcgga | gtcagtcagg | agtggcggat | cgaggagatc | 60 |
| gagctcggag | aaccggtccg | cggggaggtc | caggtccgac | tcgtggcgtc | ggggatgtgc | 120 |
| cactccgatc | accacctgcg | gaccgttggt | cgcccgattc | cgtttccctt | gagcggcggt | 180 |
| cacgaggcgt | cgggaagcgt | cacgaaggtc | ggccccgatg | tcacctctct | cgtcgagggg | 240 |
| gatgatgtgg | tgccggcgct | catcccggcg | tgcggaacct | acgggccgtg | ctcgtggggt | 300 |
| ctgcggaatc | tgtctgacga | aggtgggggg | ctgctcatcg | gtaggtccat | ctccgacggg | 360 |
| acctgccggg | cggcgcgaa | gggcgaacca | gtggtgcccg | agtgcctgct | cggcacgtta | 420 |
| tctccgtaca | tcaccggcaa | cggggcgtcg | atggcgaaga | tcgagaaaga | cattcccctc | 480 |
| gaagcttcgc | cgctgctagg | ctgcggggtg | gctaccgtgt | gggggttgggc | gaccgcgatc | 540 |
| cgcgtcacca | aggtcggtga | caccatggtt | gtcgtcggcg | tcggggggtgt | gggcatcaat | 600 |
| gccgtccagg | gcgcggctgc | cgcggggggcg | ctgcatgtca | tcgcagtcga | cccggtggag | 660 |
| ttaaagcgac | acatggccct | cgctctcggt | tcgacgcccg | tgtatgcctc | cctcggagag | 720 |
| gcggtggacc | cggtccgaga | cctgactaga | gacatgatgg | ccgacgtgac | ggtcttgacc | 780 |
| gtgagcgaca | tcgaaggcga | catcatcttg | ccggctctaa | ccatgacggc | caaggccggc | 840 |
| caggtcgtcg | tcaccgctat | gggggatgca | accaagaacg | aggtgaaact | caacctcatc | 900 |
| gagcggacgc | tgctgcagaa | gcgggtccag | tgcgccatct | tcggcggtgt | ggggccgcgc | 960 |
| accgagatcc | ccgctctcct | gcatctctat | agcagcggtg | cgctcgagct | cgaagaactc | 1020 |
| gccaccaccg | tctatcgcct | cgagcacgtc | caccagagcg | acgacgacct | cttggcgcgc | 1080 |
| gataaccagc | gcggcatcat | ccggtacacc | aacgcagact | tctga | | 1125 |

<210> SEQ ID NO 33
<211> LENGTH: 1125
<212> TYPE: DNA
<213> ORGANISM: Artificial Sequence
<220> FEATURE:
<223> OTHER INFORMATION: Description of Artificial Sequence:CddC Homolog

<400> SEQUENCE: 33

| | | | | | |
|---|---|---|---|---|---|
| atgaagacta | aggcagccgg | agaccgcgta | gatgttcagg | actggcggat | cgaaaagatc | 60 |
| gagctcgggg | atccggtcca | cggcgaggtc | caggtccgac | tcgtggcatc | gggggtgtgc | 120 |
| cactccgatc | accacctgcg | gaccgttggt | agttcgattc | catttcccgt | ggtaggcggt | 180 |
| cacgagggggt | tgggcatcgt | aaccaaggtc | ggctccggtg | tcacctctct | cgtcgagggc | 240 |
| ggtcatgcgg | tgacggcgtt | catcccgggg | tgcagaacct | gcgggccgtg | ctcgcgggct | 300 |
| ctgcaggaac | tgtgtgagga | gggtgcgtgg | ctgctcaccg | gtaggtctat | ctccgacggc | 360 |
| agctaccggg | ccagagcgaa | gggcgaacca | ctggtgcgga | agtgcctgct | cggcacgttc | 420 |
| tctccgtcca | tcaccgtcaa | cgaggcgccg | ttggtgaaga | tcgagaagga | cattcccctc | 480 |
| gaagctgcgg | cgctgctcgg | ctgggggggtg | gctacccggt | gggggttccgc | gaccgcgatc | 540 |
| ggtggcacca | aggtcggtga | caccgtggtg | gtcgccggcg | ttggaggtgt | gggcatgaat | 600 |
| gccggccagg | gggccgctgc | cgccgtggcg | cgccacgtta | acgccctcga | cccggtggag | 660 |

-continued

```
ttcaagcgac acatggccct cgcatgcggt gcgacgtccg tgtatgccgc cctcgaaggg      720
gcgatggaac cggtccggga tctgacccgg ggcctgatgc cggccgtgac ggtctttatc      780
gtgggagaca tcgtaggcga tatcattcag ccggcgctgt ccatcatggt caaggccggc      840
caggtgttcg tcaccgctat gggacacgcg acaaagaacg aggtgtcact caacctcttc      900
gagctgaagt tgttgcagaa cgggtccag gcgccatct tcggcgttct ggggccgcgc        960
accgagctgc ctggtcacct gcatcactat cgcagcggac cgctcaagct ggaggcactc     1020
gccaacaccg tctatcggct cgaggacgtc aaccagagct acgacgacaa gttgacgggc     1080
aagaacctgc gcggcctcgt caggtacacc gacgtcgact tctga                    1125
```

<210> SEQ ID NO 34
<211> LENGTH: 1125
<212> TYPE: DNA
<213> ORGANISM: Artificial Sequence
<220> FEATURE:
<223> OTHER INFORMATION: Description of Artificial Sequence:CddC Homolog

<400> SEQUENCE: 34

```
atggagacga aggcacccgt cctccgcgga gtcggtcagg actggcggat caaggagatc       60
gagctcggcg atccggttcc cgccgaggtc caggtccgac tcgtggcgtc ggggtggtgc      120
cactccgatc accacctgcg gaccggtggt agaccgattc cgtttcccgt catcggcggt      180
cacgagtggt atggcatggt caccagtgtc ggccccggtg tcccctctct cgtcgagggc      240
gatcatgtgg tgacggcgat catcccgcg tgcggaacct gcgggccgtg ctcgcggtgt       300
ctacagaagc tgtgtgacga ggctgcgggg ctgctcaccg gtaggtccat ctccgacggg      360
accttccggg cgactgcgaa gggccaacca ctggtgccga tgggcaggct cggcacgttc      420
tctccgtgca tcacctacaa ggaggcgtcg ttagtaaaga tcgagaagga cattcccctc      480
gaggctgcgg cgctcctcgg ctgctggtg gcttccgggt ggggtccggc gaccgcgatc       540
gcctgcacca cgttggtga caccgtggag gtcgtcggca tcggaggtgt gggcatcagt       600
gccgtccagg gcgcggctgc cgccggggcg ggccaagtca gtgccgtcga ccatgtggag      660
atcaatcgac acatggcgct cgcactcggt gcgacccacg tgtatgcctc ccttgtagac      720
tcgatggacc cggtcgggga ccctaccaga gtcctgaggc cggacgtgtc ggtcttgagc      780
gtgagtgaca tcaaaggcga caggatccag cccgcgctga ccatcacggc cacggctggt      840
caggtcgttg tcaccgctgt agttgacgcg acgcagaacc aggtgacact aaacctcttc      900
gagctggcgg tgccgcaaaa gcgggtccag gcgacatct tcggcggtgt ggggccgcgc       960
acccagaaca ccgctctcag gcatctccat cgcagcggcg cgctcaagct cgaggaactc     1020
gccaccacaa tctacccct ggaggtcgtc aaccagggct acgacgacat gttggcgggc      1080
aagatcctgc gcgccttctg ccggtacacc gacgccgact cctga                    1125
```

<210> SEQ ID NO 35
<211> LENGTH: 1425
<212> TYPE: DNA
<213> ORGANISM: Artificial Sequence
<220> FEATURE:
<223> OTHER INFORMATION: Description of Artificial Sequence:CddD Homolog

<400> SEQUENCE: 35

```
atgaccgatg gccattgcac ggacctctac atccacggtt cgtgggttgc ctcgacaagc       60
aagacggtaa tagaggtgcc caagcccgca accgaagagg tgatcgggac tgtcccggac      120
gggaccgcag cagatgtgga cgcggtggtg accgctgccc gggccgcggt cgtcggctgg      180
```

-continued

```
gcgagcagac cggtagtcaa gcgggcgcag tacctacaga gcatcgccgc cggcatcgcg      240
gacggcagcg acaagctgcc acgcaccatc tctgccgaga agggcgctcc gctggcgttt      300
gcccgggcca tgcgggtgcc actgcggatc aacagctgct cgcatgcagc ggccgtggcg      360
gagaccttcc cgctcgaacg caccgagggc ccatcggtcg acgtgcggga accgatcgga      420
gtggtggggg cgatcatccc gtcgaactat accccgcacc agatcgcagc gaaggtcgcc      480
tacgccttcc ccgccggaaa caccatcgtg gtgaaactga gtgaggcggc gccgctcaac      540
cccttgatgc tcgccgagat catcaatgct gcaggggttc ccgcgggcgt gttcaatctg      600
gtcagcggca cgagaccggt cgtgggtgag gtgcttgcct cccaacacga ggtggatatg      660
atatccttca ccgggtcgac caatgccggc gagagagaga gcgaactcgc cgcgcggacc      720
gtcgaacgag tcgccctaga actcggtgga acgcgcgcca agatcgtcct ggacgacgcc      780
gacctcgacg agctcatgcc gaacgcgtgg cagtgtgcaa tgatgaattc cggtcagacc      840
tgctcggctc tgacgcgcct acttgttcca cgagcgatac tcaccgcggc ggagacgacg      900
gcgatgacca tcgcggaggc ctacacggtc tgcgcaccgg acgacccgga caccacgctg      960
ggatcattgg tgtcggcgac ccagcgcaaa agggtgcgcg gctacgtcga ccgcggtgtc     1020
caggagggcg ccacgctgat cacacgcggg cgcgaaacct cgagggaat cgcggtgcgc     1080 cattacgaga agccgacgat attttcggag atgacaccacg acatgactat tcatctcgag     1140
gagatcttcg gaccggtgct atcgaacgct ccgtacgaca ccgaggagga cgcggtccgc     1200
atcgccaaag acagggagta cggctcgacg ggcggcatct ggtccaggga tgtagatcgg     1260
gcacgcgctg tcttcgcccg catgcgtacc ggacaggtga tgatcaacgg tggcgaattc     1320
tacccgaacg tgccgttcgg tggatacaag cagtcggcca ccggccggga attcgggacc     1380
catgggcgcg aagaatgcct ggaaaacaag tcgctccagt tctga                     1425
```

<210> SEQ ID NO 36
<211> LENGTH: 1425
<212> TYPE: DNA
<213> ORGANISM: Artificial Sequence
<220> FEATURE:
<223> OTHER INFORMATION: Description of Artificial Sequence:CddD Homolog

<400> SEQUENCE: 36

```
atgaccgcgg gccatttcat accgctcttc aatatcggtt cctgggttgc ctcaccaagc       60
aagacggtca tcgaggtgca caaccccgca accgaagagg tgatcggaac tgtcgcgaag      120
gggaccgcag cagatgtgga cgcggtggtg gcttctgccc gagccgcgtt ccaaggctgg      180
gcgagcacac tggtcgacaa acgcgcgcag tacttacggg gcatcgccgc cggcatcgcc      240
ggccgcaccg acgagctggc acgcaccacc tctaccgaga tgggcgctcc gctgtcgtct      300
gcccagccaa tgcaggtccc cctgccgttc aacagcttct cgcatgctgc ggccgtggcc      360
gggagcttcc ccttagaacg caccgagggc tcatcggcga acgtgcggga accgatcggg      420
gtggtggagg cgatcacccc gtggaaccat cccctgcacc agatcgccgc gaaggtcgcc      480
tacgccctcg ccgccggcaa cacgatcgtg gtgaaagcga gtgaggtcgc gccgctcaac      540
gcttggatgc tcgccgagat catcgatgcg gcagcggttc ctgcaggcgt gttcaacctg      600
gtcatcggca ccgggccggt cgtcgttgag gccctcgctt accacgacga ggtggatatg      660
atctccttca ccgggtcgac caacttcggc aagagagaga gcgaactctc gcgcagagc      720 gtcaaacgtg tcgccctcga tctcggccgc aagagcgccc acaacgtcct ggacgatgtc      780
gacatagacg agcgcatgcc taacgctgtg cagtgggcgt tgatcatttt cggtcagacc      840
```

```
tgctcctctc tgacgcgcct actactaccc cgcgcgatat tcaccgaggc ggagacggcg      900
gcgaagaact tctcggaggc ctacacggtc ggcgcaccgg acgacctgca catcacgctg      960
ggagcaatcg tttgggagac ccagctcaaa cgggtgcgac gctacatcga gcagatgtc     1020 caggcgggcg ccacgctcat cacaggcggg agcgaaaccg tcgagggaca ggcgatgggc     1080
tactacgtga agccgacggt aatttcggag gtgatccccg acaacacgat tcatcgcgag     1140
gagatcttcg gaccggtgct gtcgcacgcg ccgtacgaca ccgaggagga cgaggtccgc     1200
atcgccaacg ccatcgagca cggcttgagg ggcggcctct ggtccaggga tgtggaccgg     1260
gagcgcgctg tcgccgcccg catgctgatc ggagaggtga tgatcaacgg aggcgacttc     1320
aaccggaccg caccgttcgg tggctacaag cagtcggtcc ccggccggga attcgggccc     1380
catgggctcg aggaattcct ggaaagcaag tggatacagt tctga                     1425
```

<210> SEQ ID NO 37
<211> LENGTH: 1425
<212> TYPE: DNA
<213> ORGANISM: Artificial Sequence
<220> FEATURE:
<223> OTHER INFORMATION: Description of Artificial Sequence:CddD Homolog

<400> SEQUENCE: 37

```
atgtccgctg ccatctcac cgagctctac atcaacggtt cctgggttgc cacgacaagc       60
aagacggtga tcgaggttct cagccccgca accgaagagg tgatcgggac tgtcttggac     120
gggaccgcag cagatgtgga cgcggcgtg gcagctgccc gggccgcgtt ggacggctgg      180
gcgagctcac atgccgagaa gcgcggtcag tacctacggg ccctcgccgc cggcatcgcc     240
gaccgcagcg acgagctgac acgcaccatc tctgccgaga tgggcgctcc gctgtcggtt     300
gcacaggcta tgcaggtgcc cccgccgatc aacagcttct cgcatgcagc ggccgtggcg     360
gagatcttcc cgtctgaacg cacccagggc tcatcggtga tcttgatgga accgatcggg     420
gtggtggcgg cgatctaccc ctggaactat ccactacacc agatcgccgc gaaggtcgcc     480
gaggccctcg ccgcgggcaa caccttcgtg gtgaaaccga gtgagctggc gccgctcaac     540
ggcgggatgc tggctgagat catcgatgag gcaggggtta ccgcaggcgt gttcaatccg     600
gtcagcggca cgggaccggt cgtcgctgag ccccctagcct ttcaccacga ggatgatatg    660
ctctctttca ccgggtccac caacgccggc aagagggtga gcgaactcgc cgctctgacg     720
ttcaaacgag tcgccgtcga acctggcgga atgagcgtcg acatcgtctt ggacgacggc     780
gaccttgacg agatcatgcc gatggcggtg cactgggcga tgatcaattc cggtcatact     840
tgctcggcgc tgacgcgcgt ccgcgtaccc cggacgatag tcaccgaggc agagacggcg     900
gcgaaggccg tcggggaagc ctacacggtc ggcgaaccgg acgacccgga caccacgctg     960
ggaccagaga tgtcggcgct ccagcgcgaa cgggtgcggg gctacatcga ccgaggtgtc    1020
caggagggaa ccaccccgat gacagtcggg agcgaaaccg tcgagggact ggcggtgggc     1080
tacttcgtga agccgacgag attttcggag gtgaccccg gcatgacgat tcatcgcgag     1140
gagatcttcg gaccggttct gtcaatcgcg ccgtacgaca ccgaggagaa cgcggtccgc     1200
atcgccaacg acagcgagta cggcttgagg ggcggcgtct ggtccagaga cgtggaccgt     1260
gctcgcgctg tcgccgccgg tatgcggacc ggacaggcga tgatcaacgg tggccaattc     1320
aacgcgaacg caccgtttgg tggatatgag cggtcgggca ctggccggga atgcggggcc     1380
catgggcagg aagagttcct ggaaatagag tcgctccagt tctga                    1425
```

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 38
atgacgacga gcatcgaccg                                               20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence:Primer

<400> SEQUENCE: 39
tcagcggaag gtgaggccgt cg                                            22
```

GENES INVOLVED IN CYCLODODECANONE DEGRADATION PATHWAY

This application claims the benefit of Provisional Application No. 60/170,214 filed on Dec. 10, 1999.

FIELD OF THE INVENTION

The present invention relates to the field of molecular biology and microbiology. More particularly, the invention relates to bioproduction of dodecanoic diacid from cyclododecannone by microbiological means. The cyclododecanone degradation is mediated by a set of enzymes resident on a 10 kb gene cluster, isolated from *Rhodococcus ruber* SC1. The invention also relates to the bioproduction of lactones, hydroxy acids and diacids from cyclic compounds.

BACKGROUND OF THE INVENTION

Dodecanedioic acid (DDDA) and other diacids of different chain length are used in nylon manufacturing for production of different variants of nylon fibers. Nylon 6, 12 is a polymer condensed from monomers of hexamethylenediamine (HMD) and DDDA (C12 diacid), which has some different properties from Nylon 6,6 condensed from HMD and adipic acid (C6 diacid). The toughness of the Nylon 6,12 polymer allows it to be used in applications such as toothbrush bristles. Mixed diacids of different chain length (C11, C12 and C13) can also be used as soft segments in Lycra® or as corrosion inhibitors in automotive coatings.

Traditional ways of diacids synthesis are based on chemical and physical methods which involve harsh conditions such as very high temperatures and pressures. The chemical method to produce 1,12-dodecanoic diacid (DDDA) employs initial air oxidation of cyclododecane to yield a mixture of cyclododecanone (ketone) and cyclododecanol (alcohol), which is then oxidized to produce DDDA. Biocatalytic processes may provide an economically and environmentally more compatible approach towards nylon production. The biochemical route is performed under mild conditions such as ambient temperatures and atmospheric pressures.

Isolation of strains in the cyclododecane degradation pathway has been reported. (J. D. Schumacher and R. M. Fakoussa, *Oxidation and cleavage of alicyclic structures using bacterial biocatalysts*, DGMK Tagungsber. (1997), 9704 (Proceedings ICCS '97; Volume 3), 1583–1586. Schumacher et al., have isolated and examined the growth characteristics of *Rhodococcus ruber* $CD_1$-411 on cyclododecane as sole carbon source (Schumacher et al, supra). The authors, employing biotransformation experiments and using cyclododecane as substrate and several enzyme inhibitors, proposed that *Rhodococcus ruber* $CD_1$-411 metabolizes the alicyclic compound, cyclododecane, in a way similar to the degradation of cyclohexane. It is suggested that cyclododecane is first hydroxylated to cyclodbdecanol which is then dehydrogenated to cyclododecanone (J. D. Schumacher, et al, *Appl. Microbiol. Biotechnol*, 1999, 52:85–90). It is. postulated that this alicylic ketone is then subject to a Baeyer-Villiger oxidation yielding the lactone oxacyclotridecan-2-one (lauryl lactone), which is hydrolyzed to 12-hydroxydodecanoic acid (12-hydroxy lauric acid). Only 12-hydroxydodecanoic acid was detected by this method, under these conditions In related experiments, using an inhibitor of lactone hydrolysis, tetraethylpyrophosphate, Schumacher et al were able to detect lactone oxacyclotridecan-2-one (J. D. Schumacher, et al , *Appl. Microbiol. Biotechnol*, 1999, 52:85–90). The 12-hydroxy lauric acid was further converted to DDDA via 12-oxo lauric acid intermediate by a two-step sequential oxidation. The above proposed pathway suggests metabolic steps for the degradation of cyclododecane based on Baeyer-Villiger oxidation process and appearance of the major metabolites in *Rhodococcus ruber* CD4.

Cyclododecanone monooxygenase has been purified. This enzyme is responsible for the oxidation of cycloketone to the corresponding lactone. In spite of these findings there are no reports which describe other enzymes necessary in the cyclododecane degradation pathway. Additionally, the literature is silent with respect to genes encoding this cyclododecanone monooxygenase and isolation of the gene cluster responsible for the whole metabolic pathway.

The problem to be solved therefore is to provide a facile, environmentally responsible method for the production of dodecanoic diacid and other useful intermediates. Applicants have solved the stated problem by identifying, isolating and cloning a 10 kb nucleic acid fragment from *Rhodococcus ruber* SC1 which mediates the conversion of cyclododecanone and other cyclic compounds to dodecanoic diacid. Recombinant *Escherichia coli* hosts with the DNA containing the 10 kb gene cluster conveys on the host the ability to convert cyclododecanone to dodecanoic diacid.

SUMMARY OF THE INVENTION

The present invention provides an isolated nucleic acid fragment encoding a dodecanoic diacid synthesizing enzyme selected from the group consisting of: (a) an isolated nucleic acid fragment encoding all or a substantial portion of the amino acid sequence selected from the group consisting of SEQ ID NO:2, SEQ ID NO:4, SEQ ID NO:10, and SEQ ID NO:12; (b) an isolated nucleic acid fragment that is substantially similar to an isolated nucleic acid fragment encoding all or a substantial portion of the amino acid sequence selected from the group consisting of SEQ ID NO:2, SEQ ID NO:4, SEQ ID NO:10, and SEQ ID NO:12; (c) an isolated nucleic acid molecule that hybridizes with (a) under the following hybridization conditions: 6×SSC (1 M NaCl), 50% formamide, 1% SDS at 37° C., and a wash in 0.1×SSC at 60 to 65° C.; and (d) an isolated nucleic acid fragment that is complementary to (a), (b) or (c).

Additionally the invention provides an isolated nucleic acid fragment having about 80% to about 90% identity to the nucleic acid fragment selected from the group consisting of SEQ ID NO:1, SEQ ID NO:3, SEQ ID NO:9, SEQ ID NO:11, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, and SEQ ID NO:37.

The invention further provides polypeptides encoded by the nucleic acid sequences of the present invention. Additionally the invention provides chimeric genes comprising the instant nucleic acid sequences operably linked to suitable regulatory elements and transformed host cells comprising the chimeric genes.

In an alternate embodiment the invention provides a method of obtaining a nucleic acid fragment encoding all or a substantial portion of a dodecanoic diacid synthesizing enzyme comprising: (a) probing a genomic library with the nucleic acid fragment of the present invention; (b) identifying a DNA clone that hybridizes with the nucleic acid fragment of the present invention under the following conditions; 6×SSC (1 M NaCl), 50% formamide, 1% SDS at 37°

C., and a wash in 0.1×SSC at 60 to 65° C.; and (c) optionally sequencing the genomic fragment that comprises the clone identified in step (b), wherein the sequenced genomic fragment encodes all or substantially all of an amino acid sequence encoding a dodecanoic diacid synthesizing enzyme. Similarly the invention provides a method of obtaining a nucleic acid fragment encoding all or a substantial portion a dodecanoic diacid synthesizing enzyme comprising: (a) synthesizing at least one oligonucleotide primer corresponding to a portion of the sequence selected from the group consisting of SEQ ID NO:1, SEQ ID NO:3, SEQ ID NO:9, SEQ ID NO:11, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, and SEQ ID NO:37; and (b) amplifying an insert present in a cloning vector using the oligonucleotide primer of step (a); wherein the amplified insert encodes a portion of an amino acid sequence encoding a dodecanoic diacid synthesizing enzyme.

The invention further provides a method for the production of dodecanedioic acid comprising: contacting a transformed host cell under suitable growth conditions with an effective amount of cyclododecanone whereby dodecanedioic acid is produced, said transformed host cell comprising a nucleic acid fragment encoding SEQ ID NO:2, SEQ ID NO:4, SEQ ID NO:10, and SEQ ID NO:12 under the control of suitable regulatory sequences.

Similarly the invention provides a method for the production of lauryl lactone comprising: contacting a transformed host cell under suitable growth conditions with an effective amount of cyclododecanone whereby lauryl lactone is produced, said transformed host cell comprising a nucleic acid fragment encoding SEQ ID NO:2, under the control of suitable regulatory sequences.

Additionally the invention provides a method for the production of 12-hydroxy lauric acid comprising: contacting a transformed host cell under suitable growth conditions with an effective amount of lauryl lactone whereby 12-hydroxy lauric acid is produced, said transformed host cell comprising a nucleic acid fragment encoding SEQ ID NO:4, under the control of suitable regulatory sequences.

In another embodiment the invention provides a method for the production of 12-oxo lauric acid comprising: contacting a transformed host cell under suitable growth conditions with an effective amount 12-hydroxy lauric acid whereby 12-oxo lauric acid acid is produced, said transformed host cell comprising a nucleic acid fragment encoding SEQ ID NO:10, under the control of suitable regulatory sequences.

In an alternate embodiment the invention provides a method for the production of dodecanedioic acid comprising: contacting a transformed host cell under suitable growth conditions with an effective amount 12-oxo lauric acid whereby dodecanedioic acid is produced, said transformed host cell comprising a nucleic acid fragment encoding SEQ ID NO:12, under the control of suitable regulatory sequences.

The invention further provides an isolated nucleic acid fragment encoding a dodecanedioic acid synthesizing enzyme selected from the group consisting of: (a) an isolated nucleic acid molecule as set forth in SEQ ID NO:13; (b) an isolated nucleic acid molecule that hybridizes with (a) under the following hybridization conditions: 6×SSC (1 M NaCl), 50% formamide, 1% SDS at 37° C., and a wash in 0.1×SSC at 60 to 65° C.; and (c) an isolated nucleic acid molecule that is completely complementary to (a) or (b).

Additionally the invention provides a Rhodococcus ruber comprising endogenous genes encoding the proteins as set forth by SEQ ID NO:2, SEQ ID NO:4, SEQ ID NO:10, and SEQ ID NO:12, said Rhodococcus ruber SC1 having the ability to convert cyclododecanone to dodecanedioic acid under suitable growth conditions.

In another embodiment the invention provides a method for the production of hydroxy acids comprising: contacting a transformed host cell under suitable growth conditions with an effective amount of a cyclic ketone selected from the group consisting of C6, C10, C11, C12, C13, and C15 cyclic ketones whereby the corresponding hydroxy acid is produced, said transformed host cell comprising a nucleic acid fragment encoding SEQ ID NO:2, and SEQ ID NO:4 under the control of suitable regulatory sequences.

BRIEF DESCRIPTION OF THE DRAWINGS AND SEQUENCE DESCRIPTIONS

Figure 1:
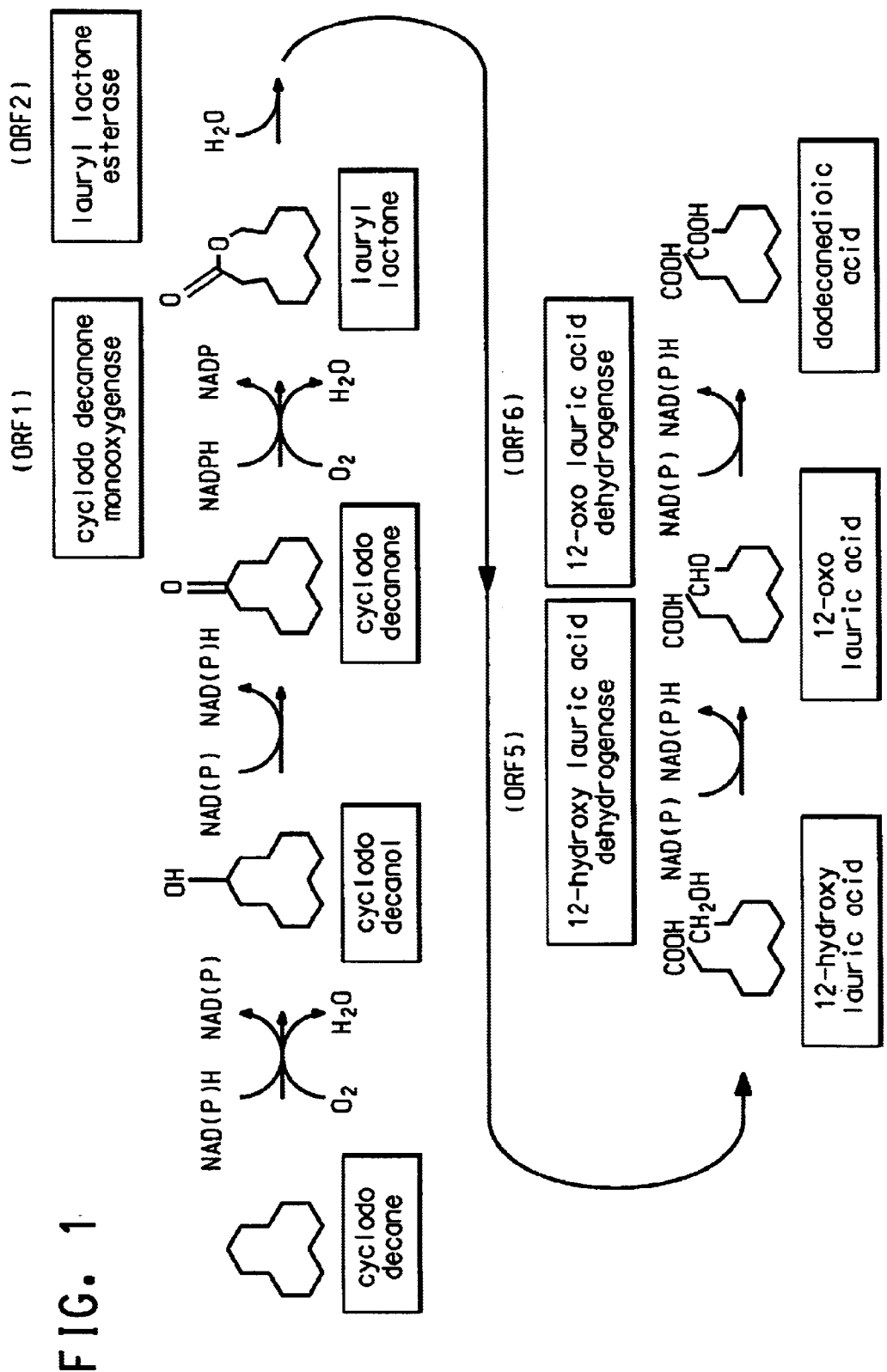
FIG. 1 is a diagram showing the pathway for the conversion of cyclododecane to dodecanoic diacid.

The invention can be more fully understood from the following detailed description and the accompanying sequence descriptions which form a part of this application.

Applicant(s) have provided 39 sequences in conformity with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence of ORF 1 encoding a cyclododecanone monooxygenase enzyme isolated from a 10 kb nucleic acid fragment from Rhodococccus ruber SC1.

SEQ ID NO:2 is the deduced amino acid sequence of ORF 1 encoding a cyclododecanone monooxygenase enzyme isolated from a 10 kb nucleic acid fragment from Rhodococccus ruber SC1.

SEQ ID NO:3 is the nucleotide sequence of ORF 2 encoding a lauryl lactone esterase enzyme isolated from a 10 kb nucleic acid fragment from Rhodococccus ruber SC1.

SEQ ID NO:4 is the deduced amino acid sequence of ORF 2 encoding a lauryl lactone esterase enzyme isolated from a 10 kb nucleic acid fragment from Rhodococccus ruber SC1.

SEQ ID. NO:5 is the nucleotide sequence of ORF 3 encoding a putative protein with unknown function isolated from a 10 kb nucleic acid fragment from Rhodococccus ruber SC1.

SEQ ID NO:6 is the deduced amino acid sequence of ORF 3 encoding a putative protein with unknown function isolated from a 10 kb nucleic acid fragment from Rhodococccus ruber SC1.

SEQ ID NO:7 is the nucleotide sequence of ORF 4 encoding a protein with unknown function isolated from a 10 kb nucleic acid fragment from Rhodococccus ruber SC1.

SEQ ID NO:8 is the deduced amino acid sequence of ORF 4 encoding a conserved hypothetical protein with unknown function isolated from a 10 kb nucleic acid fragment from *Rhodococccus ruber* SC1.

SEQ ID NO:9 is the nucleotide sequence of ORF 5 encoding a 12-hydroxy lauric acid dehydrogenase enzyme isolated from a 10 kb nucleic acid fragment from *Rhodococccus ruber* SC1.

SEQ ID NO:10 is the deduced amino acid sequence of ORF 5 encoding a 12-hydroxy lauric acid dehydrogenase enzyme isolated from a 10 kb nucleic acid fragment from *Rhodococccus ruber* SC1.

SEQ ID NO:11 is the nucleotide sequence of ORF 6 encoding a 12-oxo lauric acid dehydrogenase enzyme isolated from a 10 kb nucleic acid fragment from *Rhodococccus ruber* SC1.

SEQ ID NO:12 is the deduced amino acid sequence of ORF 6 encoding a 12-oxo lauric acid dehydrogenase enzyme isolated from a 10 kb nucleic acid fragment from *Rhodococccus ruber* SC1.

SEQ ID NO:13 is the nucleotide sequence of the 10 kb gene cluster isolated from a *Rhodococccus ruber* SC1, encoding all the enzymes relevant to the biocoversion of cyclododecanone to dodecanoic diacid.

SEQ ID NO:14 is the N-terminal amino acid sequence of cycolododecanone monooxygenase from *Rhodococccus ruber* SC1.

SEQ ID NO:15 is the internal peptide amino acid sequence of cycolododecanone monooxygenase from *Rhodococccus ruber* SC1.

SEQ ID NO:16 is the nucleotide sequence of a JCR14 primer used to sequence 16s rDNA for typing the isolated bacterium. SEQ ID NO:17 is the nucleotide sequence of a JCR15 primer used to sequence 16s rDNA for typing the isolated bacterium.

SEQ ID NO:18 is the nucleotide sequence of a CDDK4 primer which was derived from the N terminal sequence of cyclododecanone monooxygenase enzyme and was used for cloning of this enzyme from *Rhodococcus ruber* SC1.

SEQ ID NO:19 is the nucleotide sequence of a CDDK10 primer which was derived from the internal sequence of cyclododecanone monooxygenase enzyme and was used for cloning of this enzyme from *Rhodococcus ruber* SC1.

SEQ ID NO:20 is the nucleotide sequence of a C12 MO TOP primer which was used to screen the cosmid library.

SEQ ID NO:21 is the nucleotide sequence of a C12 MO BOTTOM primer which was used to screen the cosmid library.

SEQ ID NO:22 is the nucleotide sequence of a KK1 primer used to construct a subclone pDCQ5 containing only cyclododecanone monooxygenase gene and lauric acid esterase gene.

SEQ ID NO:23 is the nucleotide sequence of a KK2 primer used to construct a subclone pDCQ5 containing only cyclododecanone monooxygenase gene and lauric acid esterase gene.

SEQ ID NO:24 is the nucleotide sequence of a KK3 primer used to construct a subclone pDCQ6 containing only cyclododecanone monooxygenase gene and lauric acid esterase gene.

SEQ ID NO:25 is the nucleotide sequence of a KK4 primer used to construct a subclone pDCQ6 containing only cyclododecanone monooxygenase gene and lauric acid esterase gene.

SEQ ID NOs:26–28 are nucleic acid sequences which will hybridize under stringent conditions to the nucleic acid sequence for ORF 1 (SEQ ID NO:1) encoding a cyclododecanone monooxygenase enzyme.

SEQ ID NOs:29–31 are nucleic acid sequences which will hybridize under stringent conditions to the nucleic acid sequence for ORF 2 (SEQ ID NO:3) encoding a lauryl lactone esterase enzyme.

SEQ ID NOs:32–34 are nucleic acid sequences which will hybridize under stringent conditions to the nucleic acid sequence for ORF 5 (SEQ ID NO:9) encoding a 12-hydroxy lauric acid dehydrogenase enzyme.

SEQ ID NOs:35–37 are nucleic acid sequences which will hybridize under stringent conditions to the nucleic acid sequence for ORF 6 (SEQ ID NO:11) encoding a 12-oxo lauric acid dehydrogenase enzyme.

SEQ ID NOs:38–39 are primers used to amplify the cddA gene.

DETAILED DESCRIPTION OF THE INVENTION

Figure 2:
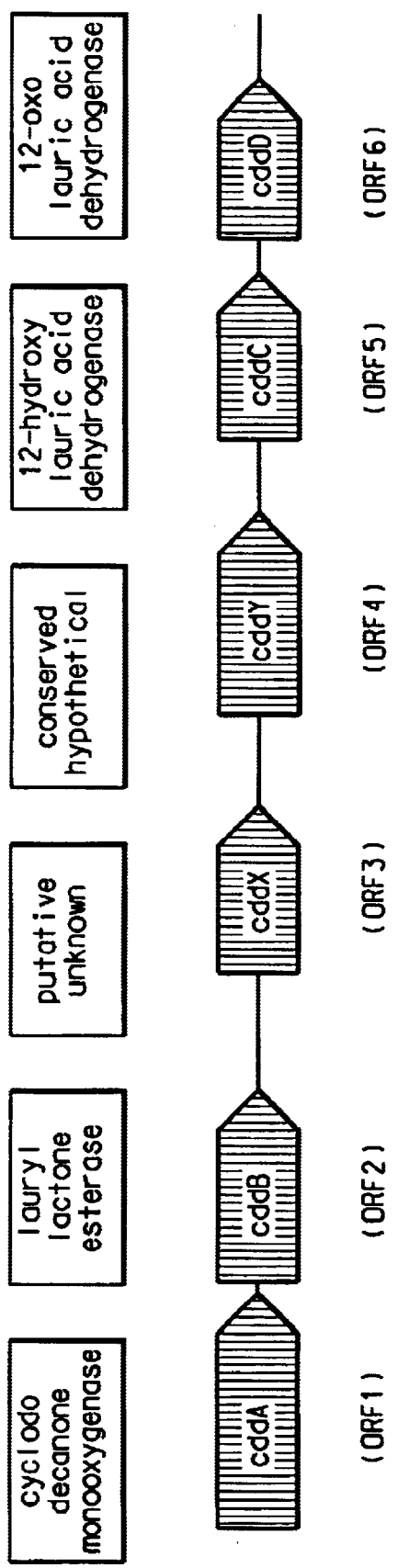
FIG. 2 is a diagram showing the organization of ORF's 1–6 on the 10 kb gene cluster.

The present invention provides new sequences encoding key enzymes in the synthesis of dodecanoic diacid from cyclododecanone. The genes and their expression products are useful for the creation of recombinant organisms that have the ability to produce dodecanoic diacid while growing on cyclododecanone, and for the identification of new species of bacteria having the ability to produce dodecanoic diacid. Dodecanedioic acid (DDDA) and other diacids have utility as monomers in the manufacture of various polymers such as Nylon. Other intermediates such as lactones have utilities as automotive coatings or flavors and fragrances. Full length sequences for 6 ORF's have been obtained and identified by comparison to public databases containing nucleotide and protein sequences using the BLAST algorithms well known to those skilled in the art. The relevant ORF's all reside on a 10 kb nucleic acid fragment and together represent a gene cluster that encodes proteins that are sufficient to mediate the transformation of cyclododecanone to dodecanoic diacid (FIGS. 1 and 2). The genes involved in cyclododecanone oxidation have been isolated from *Rhodococcus ruber* SC1. Conversion of cyclododecanone to dodecanoic diacid has been demonstrated in recombinant host cells containing the 10 kb nucleic acid fragment. Moreover, it has been discovered that the enzymes involved in cyclododecanone degradation pathway have specificity for large cyclic ketones. For example, hydroxy acids of C6, C10 C11, C12, C13, and C15 were produced from their corresponding cyclic ketones. The hydroxy acids of the present invention have use as monomers in the synthesis of polymers such as polyester.

In this disclosure, a number of terms and abbreviations are used. The following definitions are provided.

"Open reading frame" is abbreviated ORF.

"Polymerase chain reaction" is abbreviated PCR.

"High performance liquid chromatography" is abbreviated HPLC.

"Mass spectrometry" is abbreviated MS.

"High performance liquid chromatography coupled with mass spectrometry" is abbreviated LC/MS.

"Baeyer-Villiger oxidation" refers to a reaction of oxidizing carbonyl compounds by peroxy compounds which involves formal insertion of an oxygen atom into one of the carbon-carbon bonds at the carbonyl group. This insertion is accomplished by a sequence of steps involving addition of the carbonyl group and migration to oxygen.

"Cyclododecanone monooxygenase" refers to the enzyme required in the oxidation of cycloketone to the corresponding lactone. This enzyme is encoded by ORF 1 (designated as cddA) and is resident on the 10 kb *Rhodococcus ruber* SC1 gene cluster, necessary for the conversion of cyclododecanone to dodecanoic diacid.

"Lauryl lactone esterase" or "lauryl lactone hydrolase" refers to an enzyme that is involved in the conversion of lauryl lactone to 12-hydroxy lauric acid. This enzyme is encoded by ORF 2 (designated as cddB) and is resident on the 10 kb *Rhodococcus ruber* SC1 gene cluster, necessary for the conversion of cyclododecanone to dodecanoic diacid.

"12-hydroxy lauric acid dehydrogenase" refers to an alcohol dehydrogenase enzyme that catalyzes oxidation of 12-hydroxy lauric acid to 12-oxo lauric acid. This enzyme is encoded by ORF 5 (designated as cddC) and is resident on the 10 kb *Rhodococcus ruber* SC1 gene cluster, necessary for the conversion of cyclododecanone to dodecanoic diacid.

"12-oxo lauric acid dehydrogenase" refers to an aldehyde dehydrogenase which catalyzes conversion of I12-oxo lauric acid to dodecanoic diacid. This enzyme is encoded by ORF 6 (designated as cddD) and is resident on the 10 kb *Rhodococcus ruber* SC1 gene cluster, necessary for the conversion of cyclododecanone to dodecanoic diacid.

The term "cddX" and "cddY" refers to two unknown proteins encoded by ORF 3 and ORF 4, respectively, both of which are resident on the 10 kb *Rhodococcus ruber* SC1 gene cluster, necessary for the conversion of cyclododecanone to dodecanoic diacid.

The term: "gene cluster" will mean genes organized in a single expression unit or physically associated with each other.

The term "10 kb nucleic acid fragment" refers to the 10 kb gene cluster comprising ORFs 1–6 sufficient for the conversion of cyclododecanone to dodecanoic diacid.

The term "dodecanoic diacid" and "dodecanedioic acid" will be used interchangeably and abbreviated as DDDA.

The term "dodecanoic diacid synthesizing enzyme" means the gene product of any of ORF 1, ORF 2, ORF 5 and ORF 6 encoding SEQ ID NO:2, SEQ ID NO:4 SEQ ID NO:10 and SEQ ID NO:12, respectively.

The term "knockout construct" means a DNA sequence which has been altered via any known means, for example, insertion, deletion, point mutation or rearrangement, so as to eliminate the function of one or more of the naturally occurring gene products.

The term "knockout mutants" refer to cells, microorganisms in which one or more of the naturally occurring genes have been replaced through genetic engineering with a knockout construct.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions, (0.1×SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 6×SSC (1 M NaCl), 30 to 35% formamide, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 6×SSC (1 M NaCl), 40 to 45% formamide, 1% SDS at 37° C., and a wash in 0.5× to 1×SSC at 55 to 60° C. Exemplary high stringency conditions include hybridization in 6×SSC (1 M NaCl), 50% formamide, 1% SDS at 37° C., and a wash in 0.1×SSC at 60 to 65° C.

Specificity is typically the function of post-hybridization washes, the critical factors being the ionic strength and temperature of the final wash solution. The melting temperature ($T_m$) of a probe-target hybrid can be calculated to provide a starting point for the determination of correct stringency conditions. For DNA-DNA hybrids, the $T_m$ can be approximated from the equation of Meinkoth and Wahl, Anal. Biochem., 138:267–284 (1984): $T_m$=81.5° C.+16.6 (log M)+0.41 (%G+C)−0.61 (% form)−500/L; where M is the molarity of monovalent cations, %G+C is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. Thus, for example, sequences that will hybridize to the nucleic acid sequence of ORF 1 (SEQ ID NO:1) under stringent conditions will include but are not limited to those sequences set forth in SEQ ID NOs:26–28. Those sequences that will hybridize to the nucleic acid sequence of ORF 2 (SEQ ID NO:3) under stringent conditions will include but are not limited to those sequences set forth in SEQ ID NOs:29–31. Those sequences that will hybridize to the nucleic acid sequence of ORF 5 (SEQ ID NO:9) under stringent conditions will include but are not limited to those sequences set forth in SEQ ID NOs:32–34. Similarly, those sequences that will hybridize to the nucleic acid sequence of ORF 6 (SEQ ID NO:11) under stringent conditions will include but are not limited to those sequences set forth in SEQ ID NOs:35–37. An extensive guide to the hybridization of nucleic acids is found in Tijssen, *Laboratory Techniques in Biochemistry and Molecular Biology— Hybridization with Nucleic Acid Probes*, Part 1, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically:identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but-not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et. al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, NY). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Codon degeneracy" refers to divergence in the genetic code permitting variation of the; nucleotide sequence without effecting the amino acid sequence of an encoded polypeptide. Accordingly, the instant invention relates to any nucleic acid fragment that encodes all or a substantial portion of the amino acid sequence encoding the bacterial dodecanoic diacid synthesizing enzymes as set forth in SEQ ID NO:2, SEQ ID NO:4, SEQ ID NO:10, and SEQ ID NO:12.

The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art as described by Sambrook, J., Fritsch, E. F. and Maniatis, T., Molecular Cloning: A Laboratory Manual, Second Edition, Cold Spring Harbor Laboratory Press, Cold Spring Harbor, NY (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, NY (1984); and by Ausubel, F. M. et al., Current Protocols in Molecular Biology, published by Greene Publishing Assoc. and Wiley-Interscience (1987).

The invention provides new sequences encoding key enzymes in the synthesis of dodecanoic diacid from cyclododecanone. These sequences comprising six open reading frames residing on a 10 kb gene cluster isolated from *Rhodococcus ruber* SC1. ORF's 1, 2, 5 and 6 all encode identifiable enzymes known to be useful in the synthesis of DDDA. The present genes were identified both on the basis of expression data as well as comparison of the nucleic acid and deduced amino acid sequences to public databases using algorithms well known in the art. Sequence comparisons revealed that the most similar known sequences range from a distant as about 30% identical at the amino acid level (ORF 1, cyclohexanone monooxygenase) to about 50% identical (ORF 2, 12-oxo lauric acid dehydrogenase).

Accordingly preferred polypeptides of the instant invention are those active proteins which are at least 80% identical to the amino acid sequence of reported herein. More preferred amino acid fragments are at least 90% identical to the sequences herein. Most preferred are nucleic acid fragments that are at least 95% identical to the amino acid fragments reported herein. Similarly, preferred nucleic acid sequences corresponding to the instant ORF's are those encoding active proteins and which are at least 80% identical to the nucleic acid sequences of reported herein. More preferred nucleic acid fragments are at least 90% identical to the;sequences herein. Most preferred are nucleic acid fragments that are at least 95% identical to the nucleic acid fragments reported herein.

The nucleic acid fragments of the instant invention may be used to isolate cDNAs and genes encoding homologous enzymes from the same or other bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding similar enzymes to those of the instant dodecanoic diacid pathway, either as cDNAs or genomic DNAs, could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

Where PCR is employed, two short segments of the instant ORF's 1–6 may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding bacterial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Only part of the probe molecule need be complementary to the nucleic acid sequence to be detected. In addition, the complementarily between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kilodaltons), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. *Adv. Immunol.* 36:1 (1984); Maniatis).

The enzymes and gene products of the instant 10 kb nucleic acid fragment may be produced in heterologous host cells, particularly in the cells of microbial hosts, and can be used to prepare antibodies to the resulting proteins by methods well known to those skilled in the art. The antibodies are useful for detecting the proteins in situ in cells or in vitro in cell extracts. Preferred heterologous host cells for production of the instant enzymes are microbial hosts. Specific suitable hosts include but are not limited Aspergillus, Saccharomyces, Pichia, Candida, Hansenula, Salmonella, Bacillus, Acinetobacter, Rhodococcus, Streptomyces, Escherichia, Corynebacterium, and Pseudomonas. Microbial expression systems and expression vectors containing regulatory sequences that direct high level expression of foreign proteins are well known to those skilled in the art. Any of these could be used to construct chimeric genes for production of the any of the gene products of the 10 kb fragment. These chimeric genes could then be introduced into appropriate microorganisms via transformation to provide high level expression of the enzymes.

Additionally, chimeric genes will be effective in altering the properties of the host bacteria. It is expected, for example, that introduction of chimeric genes encoding one or more of the ORF's 1–6 under the control of the appropriate promoters, into a host cell comprising at least one copy of these genes will demonstrate the ability to convert cyclododecanone to lauryl lactone; lauryl lactone to 12-hydroxy lauric acid; and 12-hydroxy lauric acid to 12-oxo lauric acid and 12-oxo lauric acid to DDDA respectively. Additionally expression of ORF's 1–6, either separately or together may facilitate the mediation of cyclododecanone to dodecanoic diacid, or any of the intermediate steps depending on the presence or absence of these proteins in the host. Applicants have discovered that the instant dodecanoic diacid synthesizing enzymes have a broad substrate specificity and are able to act on cyclic ketones and esters ranging from C6 to C18 where a range of C6 to C15 is preferred. Accordingly it is contemplated that microbial hosts transformed with genes encoding the instant enzymes will demonstrate the ability to convert C6–C18 cyclic ketones and preferably C6, C10–C13 and C15 cyclic ketones and esters to their corresponding hydroxy acids. For example cyclohexanone (C6), cyclodecanone (C10), cycloundecanone (C11), cyclododecanone (C12), cyclotridecanone (C13) and cyclopentadecanone (C15) may each be converted to their corresponding hydroxy acids in the presence of the instant dodecanoic diacid synthesizing enzymes. Additionally it will be appreciated by the skilled person that, given the broad substrate range of the present enzymes it is contemplated that these proteins will convert cyclic ketones to macrolactones of C10 or greater.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, trp, $IP_L$, $IP_R$, T7, tac, and trc (useful for expression in Escherichia coli).

Termination control regions may also be derived from various genes native to the preferred hosts. Optionally, a termination site may be unnecessary however; it is most preferred if included.

Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (see for example EP 546049; WO 9324631). The secretion signal DNA may be between the expression-controlling DNA and the instant gene or gene fragment, and in reading frame with the latter. Where commercial production of dodecanoic diacid or any of the intermediates in the synthesis of dodecanoic diacid from cyclododencane using organisms transformed with the instant genes is desired, a variety of fermentation methodologies may be applied. For example, large scale production may be produced by both Batch or continuous fermentation.

Classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in Biotechnology: A Textbook of Industrial Microbiology, Second Edition (1989) Sinauer Associates, Inc., Sunderland, M. A., or Deshpande, Mukund V., Appl. Biochem. Biotechnol., 36, 227, (1992), herein incorporated by reference.

Commercial production of dodecanoic diacid and related synthesis intermediates may also be accomplished with continuous fermentation. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present nucleotides may be used to produce gene products having enhanced or altered activity. Various methods are known for mutating a native gene sequence to produce a gene product with altered or enhanced activity including but not limited to error prone PCR (Melnikov et al., *Nucleic Acids Research*, (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San-Diego, Calif.) and "gene shuffling" (U.S. Pat. Nos. 5,605, 793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction of a gene of interest into fragments of specific size in the presence of additional populations of DNA regions of both similarity to or difference to the gene of interest. This pool of fragments was then denatured and then reannealed to create a mutate gene. The mutated gene is then screened for altered activity.

The instant bacterial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant bacteria sequences populations of fragments that are hybridizable to all or portions of the bacterial sequence may added. Similarly, a population of fragments which are not hybridizable to the instant sequence may also be added. Typically these additional fragment populations are added in about 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded-nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100C. Nucleic acid fragments may be reannealed by cooling. Preferably the temperature is from 20° C. to 75° C. Renaturation can be accelerated by the addition of polyethylene glycol ("PEG") or salt. The salt concentration is preferably from 0 mM to 200 mM. The annealed nucleic acid fragments are next incubated in the presence of a nucleic acid polymerase and dNTP's (i.e. dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide of from about 50 bp to about 100 kb and may be screened for expression and altered activity by standard cloning and expression protocol. (Manatis supra).

DESCRIPTION OF THE PREFERRED EMBODIMENTS

The present invention relates to the isolation of genes encoding enzymes useful for the conversion of cyclododecanone to dodecanoic diacid. The relevant genes were isolated from a *Rhodococcus ruber* SC1 which was cultured from an industrial waste stream. Colonies that had the ability to grow on cyclododecanone as a sole carbon source were selected for further study.

To facilitate the isolation of the present gene cluster the clyclododecanone monooxygenase was isolated and purified from the *Rhodococcus ruber* SC1 strain on the basis of a substrate-dependent NADPH oxidation assay. Following purification the N-terminal sequence of the protein was determined by standard peptide sequencing methods.

Using the N-terminal sequence of the monooxygenase, the gene was recovered from the isolated *Rhodococcus ruber* SC1 genome in a cosmid. Sequencing of the cosmid revealed the gene sequence of the monooxygenase and the other associated ORF's encoding the remaining dodecanoic diacid synthesizing enzymes (ORF's 2–6). All the relevant ORF's resided on a 10 kb portion of the cosmid and the entire 10 kb region was sequenced.

Transformation-studies revealed that 12-hydroxy lauric acid and dodecanoic diacid were synthesize in the presence of cyclododecanone by organisms transformed with the cosmid. Additionally it was demonstrated that lauryl lactone was accumulated in a recombinant organism comprising a plasmid subclone where the downstream gene (ORF 2, encoding the lauryl lactone esterase) was disrupted.

Further studies of enzyme kinetics indicated that the dodecanoic diacid synthesizing enzymes, acting in concert, had substrate specificities beyond their natural substrates. When cosmid transformants were grown in the presence of cyclic ketones ranging from C6–C15, good conversion to the corresponding hydroxy acids was seen.

EXAMPLES

The present invention is further defined in the following Examples presenting the details of the procedures that were followed in its development and validation. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, NY (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, DC. (1994)) or by Thomas D. Brock in Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCOJBRL (Gaithersburg, Md.), or Sigma Chemical Company (St. Louis, Mo.) unless otherwise specified.

Manipulations of genetic sequences were accomplished using the BLAST family of programs which can be used for database similarity searches. The family includes BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995). Software for performing BLAST analyses is publicly available, e.g., through the National Center for Biotechnology Information (http://www.ncbi.nlm.nih.gov/) and other sources (BLAST Manual, Altschul et al., Natl. Cent. Biotechnol. Inf., Natl. Library Med. (NCBI NLM) NIH, Bethesda, Md. 20894; Altschul et al., *J. Mol. Biol.* 215:403–410 (1990)). Unless otherwise stated all sequence analysis algorithms employed default values.

The meaning of abbreviations is as follows: "h" means hour(s), "min" means minute(s), "sec", means second(s), "d" means day(s), "mL" means milliliters, "L" means liters.

Bacterial Strains and Plasmids:

*Rhodococcus ruber* SC1 was isolated from enrichment of activated sludge obtained from an industrial wastewater treatment facility. *Escherichia coli* XL1-BlueMR and SuperCos 1 cosmid vector were purchased as part of the SuperCos 1 Cosmid Vector Kit from Stratagene (La Jolla, Calif.). pBluescript SK(+) vector was also purchased from Stratagene. Shot-gun cloning vector pUC18 treated with SmaI/ BAP was purchased from GIBCO/BRL.

Growth Conditions:

Bacterial cells were usually grown in Luria-Bertani medium containing 1% of bacto-tryptone, 0.5% of bacto-yeast extract and 1% of NaCl unless otherwise indicated below.

Synthetic S12 medium was used to establish enrichment. S12 medium contains the following: 10 mM ammonium sulfate, 50 mM potassium phosphate buffer (pH 7.0), 2 mM $MgCl_2$, 0.7 mM $CaCl_2$, 50 $\mu$M $MnCl_2$, 1 $\mu$M $FeCl_3$, 1 $\mu$M $ZnCl_3$, 1.72 $\mu$M $CuSO_4$, 2.53 $\mu$M $CoCl_2$, 2.42 $\mu$M $Na_2MoO_2$, and 0.0001% $FeSO_4$. The carbon sources were added directly to the S12 medium and the bacteria were grown in sealed culture flasks.

S12 agar was used to test isolates that utilize compounds as the sole source of carbon and energy. S12 agar was prepared by adding 1.5% Noble agar (DIFCO) to S12 medium. Bacteria growing on S12 agar were supplied with volatile compounds such as cyclododecanone by sprinkling solids of the volatile compound on the interior of the petri dish lid or 5 $\mu$l of other volatile liquid as vapor. The petri dish was sealed with parafilm and incubated with the lid on the bottom.

The standard M9 minimal medium was used to assay for dodecanoic diacid and/or intermediates production from recombinant *E. coli* clones. The M9 medium consisted of 42.3 mM $Na_2HPO_4$, 22.1 mM $KH_2PO_4$, 8.6 mM NaCl, 18.7 mM $NH_4Cl$, 2 mM $MgSO_4$, 0.1 mM $CaCl_2$. 0.4% of glucose was used as the carbon source. 250 mg/l of cyclododecanone was added as the substrate for bioconversion.

Construction of Rhodococcusr Cosmid Library:

*Rhodococcus ruber* SC1 was grown in 25 mL LB medium till mid-log phase at 37° C. with aeration. Bacterial cells were centrifuged at 6,000 rpm for 10 min in a Sorvall RC5C centrifuge at 4° C. Supernatant was decanted and cell pellet was frozen at –80° C. Chromosomal DNA was prepared as outlined below with special care taken to avoid shearing of DNA. The cell pellet was gently resuspended in 5 mL of 50 mM Tris-10 mM EDTA (pH 8) and lysozyme was added to a final concentration of 2 mg/mL. The suspension was incubated at 37° C. overnight. Sodium dodecyl sulfate was then added to a final concentration of 1% and proteinase K was added at 100 $\mu$g/mL final concentration. The suspension was incubated at 55° C. for 5 h. The suspension became clear and the clear lysate was extracted with equal volume of phenol:chloroform:isoamyl alcohol (25:24:1). After centrifuging at 17,000 g for 20 min, the aqueous phase was carefully removed and transfered to a new tube. Two volumes of ethanol were added and the DNA was gently spooled with a sealed glass pasteur pipet. The DNA was dipped into a tube containing 70% ethanol. After air drying, the DNA was resuspended in 400 $\mu$l of TE (10 mMTris-1 mM EDTA, pH 8) with RNaseA (100 $\mu$g/mL) and store at 4° C. The concentration and purity of DNA was determined spectrophotometrically by OD260/OD280. A diluted aliquot of DNA was run on a 0.5% agarose gel to determine the intact nature of DNA.

Chromosomal DNA was partially digested with Sau3AI (GIBRO/BRL, Gaithersburg, Md.) as outlined by the instruction manual for the SuperCos 1 Cosmid Vector Kit. DNA (10 $\mu$g) was digested with 0.5 unit of Sau3AI at room temperature in 100 $\mu$l of reaction volume. Aliquotes of 20 $\mu$l were withdrawn at various time points of the digestion: e.g., 0, 3, 6, 9, 12 min. DNA loading buffer was added and samples were analyzed on a 0.5% agarose gel to determine the extent of digestion. A decrease in size of chromosomal DNA corresponded to an increase in the length of time for Sau3AI digestion. The larger scale preparative reaction was performed using 50 $\mu$g of DNA digested with 1 unit of Sau3AI for 3 min. at room temperature. The digestion was terminated by addition of EDTA to 8 mM final concentration. The DNA was extracted once with phenol:chloroform:isoamyl alcohol and once with chloroform. The aqueous phase was adjusted to 0.3 M NaOAc and ethanol precipitated. The partially digested DNA was dephosphorylated with calf intestinal alkaline phosphatase (Gibco/BRL) and ligated to SuperCos 1 vector, which had been treated according to the instructions in the SuperCos 1 Cosmid Vector Kit. The ligated DNA was packaged into lambda phage using Gigapack III XL packaging extract recommended by Stratagene. Manufacturer's instructions were followed. The packaged Rhodococcus genomic DNA library contained a phage titer of $1 \times 10^5$ colony forming units per $\mu$g of DNA as determined by transfecting *E. coli* XL1-Blue MR (Stratagene). Cosmid DNA was isolated from twelve randomly chosen *E. coli* transformants and found to contain large insert of DNA (30–40 kb).

Construction of Shot-gun Sequencing Library:

Cosmid DNA with large DNA insert was sheared in a nebulizer (Inhalation Plastics Inc., Chicago, Ill.) at 20 psi for 45 sec and the 1–3 kb portion was gel purified. Purified DNA was treated with T4 DNA polymerase and T4 polynucleotide kinase following manufacturer's (GIBCO/BRL) instructions. Polished inserts were ligated to pUC18 vector using Ready-To-Go pUC18SmaI/BAP+Ligase (GIBCO/BRL). The ligated DNA was transformed into *E. coli* DH5α cells (Gibco/BRL) and plated on LB with ampicillin and X-gal. Majority of the transformants was white and those containing inserts were sequenced with the universal and reverse primers of pUC18 by standard sequencing methods. ps Southern Hybridization:

Southern hybridization was used to map the junction of the insert DNA in cosmids. Cosmid DNA was digested with single restriction enzyme such as BglII, NcoI or XhoI. The digests were separated on a 0.9% agarose gel and transferred to positively charged Nylon membrane (Boehringer Mannheim, Indianapolis, Ind.) by alkaline downward capillary blotting. Probes for cyclododecanone monooxygenase gene and the alcohol dehydrogenase gene were prepared with PCR DIG labeling kit (Boehringer Mannheim) using digoxigenin-labeled dNTP. Hybridization was carried out overnight at 37° C. in Easy Hyb Solution (Boehringer Mannheim). The blot was washed once with 2×SSC+0.1% SDS and once with 0.1×SSC+0.1% SDS and developed with DIG-luminescent detection kit (Boehringer Mannheim).

Isolation and Identification of Dodecanoic Diacids or Intermediates:

Transformed XL I-Blue MR cells were grown in M9 medium with 0.4% glucose as sole carbon source. Substrate for conversion was added at early log phase (OD=0.2) and cells were allowed to grow at 30° C. for 20 additional hours. Cells were then frozen and thawed once, centrifuged, and supernatant was filtered through 0.2 $\mu$m filters. Filtrate was prepared for GC/MS analysis as described below.

Filtrate was first acidified to pH 2 using concentrated HCl. The acidified sample was extracted twice with methylene chloride or ethyl acetate. The extracts were combined and dried by adding anhydrous magnesium sulfate. Magnesium sulfate was then removed by filteration using Whatman 3MM filter paper and the remaining solvent in the filtrate was evaporated under a gentle stream of nitrogen. The dried residues were resuspended in 0.5 mL of methylene chloride as underivatized samples or derivatized with 0.5 mL of BSTFA [bis (trimethylsilyl) trifluoroacetamide] silylation reagent (SUPELCO, Bellefonte, Pa.). The GC/MS analysis was performed using a Hewlett Packard 5989B MS Engine GC/MS instrument. Samples were injected onto a 30 meter MDN-55 capillary column (SUPELCO, 0.5 $\mu$m film thickness) for separation. GC/MS analysis was conducted using electron impact ionization (70 eV).

Example 1

Isolation and Identification of a Bacterium That Grows With Cyclododecanone as Sole Source of Carbon and Energy Bacterial strains that could grow on cyclododecanone as the sole source of carbon and energy were isolated. Analysis of 16s rRNA gene sequences indicated that the collection of isolates belong to the the bacterial genus Rhodococcus.

Bacterial strains that grew on cyclododecanone were isolated from an enrichment culture. The enrichment culture was established by inoculating 1 mL of activated sludge into 20 mL of S12 medium in a 125 mL screw-cap Erlenmeyer flask. The activated sludge was obtained from a wastewater treatment facility. The enrichment culture was supplemented with flakes of cyclododecanone, added directly to the culture medium and was incubated at 35° C. with reciprocal shaking. The enrichment culture was maintained by adding cyclododecanone flakes every 4–6 days. The culture was diluted every 5–11 days by replacing 18 mL of the culture with the same volume of S12 medium. After 24 days of incubation, 100 $\mu$l of the enrichment culture was spread onto S12 plates with cyclododecanone as the carbon source. Bacteria that grew on the S12/cyclododecanone plates were purified by streaking onto R2A agar media (DIFCO Laboratory, Detroit, Mich.). A single colony, designated as SC1, was isolated and it was able to grow on S12 liquid with cyclododecanone as the sole carbon and energy source.

Strain SC1 was typed using 16s rRNA gene sequence analysis as follows. SC1 was grown on R2A agar. Several colonies from the plate were suspended in 200 $\mu$l of TE+RNase and 0.1 mg/mL of lysozyme, and incubated 37° C. for 4 hrs. To this mixture Proteinase K and SDS were added to final concentration of 50 $\mu$g/mL of and 0.5%, respectively. The mixture was extracted with phenol/chloroform and precipitated with sodium acetate and ethanol. The 16s rRNA gene sequences in the suspension were amplified by PCR by using a commercial kit according to the manufacturer's instructions (Perkin Elmer, Norfolk, Conn.) with JCR14 primer ACGGGCGGTGTGTAC (SEQ ID NO:16) and JCR15 primer GCCAGCAGCCGCGGTA (SEQ ID NO:17). PCR was performed in a Perkin Elmer GeneAmp 9600. The samples were incubated for 5 min at 94° C. and then cycled 35 times at 94° C. for 30 sec, 55° C. for 1 min and 72° C. for 1 min. The amplified 16s rRNA genes were purified using a QIAquick PCR Purification Kit according to the manufacturer's instructions (Qiagen, Valencia, Calif.) and sequenced on an automated ABI sequencer. The 16s rRNA gene sequence of strain SC1 was used as the query sequence for a BLASTN search (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389–3402. The isolate has close homology to *Rhodococcus ruber*, and designated as *R. ruber* strain SC1.

*Rhodococcus ruber* SC1 isolated from cyclododecanone (C12 cyclic ketone) enrichment culture was also tested for growth on cyclic ketones of different carbon numbers as sole carbon and energy source (Table 3). It grows well on cyclopentadecanone (C15 cyclic ketone), cyclotridecanone (C13 cyclic ketone), cyclododecanone (C12 cyclic ketone) and cycloundecanone (C11 cyclic ketone). It grows moderately well on cyclodecanone (C10 cyclic ketone). It does not grow on cyclooctanone (C8 cyclic ketone), cycloheptanone (C7 cyclic ketone) and cyclohexanone (C6 cyclic ketone).

Example 2

Purification and Characterization of Cyclododecanone Monooxvgenase Enzyme From Rhodococcus Ruber SC1

Purification of Cyclododecanone Monooxygenase:

One liter of LB in a 2.8 L Fembach flask was inoculated with *Rhodococcus ruber* SC1 (100 mL LB culture grown overnight) and allowed to grow at 37° C. with shaking for about 24 h. Cells were collected by centrifugation (11000×g, 20 min) in sterile bottles, washed twice with S12+10 mg/L yeast extract medium (S12+YE, 200 mL), and added to S12+YE (1 L), supplemented with about 8–10 mg of solid cyclododecanone, and allowed to grow at 37° C. overnight. A second portion of cyclododecanone was added in the morning, and the culture was allowed to grow for 6–8 h longer. The cells were then collected by centrifugation. A typical culture provided 5–7 g of cell paste.

The above cell paste was suspended in 40 mL of 50 mM Na-HEPES buffer (N-2-hydroxyethyl piperazine-N'-2-ethanesulfonic acid, pH 7.5). About two mg of lysozyme was added, and the suspension was kept at 0C for 0.5 to 2 h. 0.2 mL of PMSF stock solution (phenylmethylsulfonyl fluoride, 0.1 M in ethanol) was added and the suspension was passed seven times through a French press at 16000 psi. PMSF was added again as before, and the extract was centrifuged (9000×g, 20 min). The supernatant was set aside as the crude cell extract. The pellet was suspended in 20 mL of HB buffer (50 mM Na-HEPES, pH 7.5, +10 mM 2-mercaptoethanol), and centrifuged as before. The crude cell extracts were combined, diluted with HB to 250 mL, and applied to Pharmacia Q-Sepharose fast flow column (column volume: 100 mL in HB, run at 4° C.). The column was washed with HB (100 mL) and eluted with a linear NaCl gradient (0 to 0.7 M NaCl in HB, 500 mL each with 2.4 mL/min flow rate). Activity of fractions were determined by NADPH oxidation assay. Active fractions were pooled (typically ~40 mL) and diluted with HB (total volume ~200 mL), and applied to an Amicon Matrex Red A agarose column (column volume: 5 mL in HB, run at 4° C., Beverly, Mass.). The red agarose affinity column is designed for enzymes requiring NADPH as cofactor [Branchaud and Walsh, *J. Am. Chem. Soc.* 107, 2153–2161 (1985)]. The column was washed with 15 mL of HB, and monoxygenase was eluted with 25 mL of NADPH (0.1 mM). Further purification was obtained by gel filtration with TSK-3000SW column (TosoHaas, Montgomeryville, Pa.) using HB buffer at 0.5 mL /min flow rate or by Reverse Phase-HPLC using Vydac C-4 column (4.6×250 mm, The Separation Group, Hesperia, Calif.) using water+0.1% TFA (A) and acetonitrile+0.1% TFA (B) gradient at flow:rate of 1 mL/min. The gradient was set as follows: 0 min, 25% B; 5 min, 25%B; 14 min, 43%B; 54 min, 51%B; 54.1 min, 90%B; 59 min, 90%B. A typical load was ~0.5 mg protein.). Protein eluted from the affinity column was typically >90% pure when examined by SDS-PAGE, and the yield was on the order of ~0.02 mg per g of cell paste. The size of the protein was estimated to be 65–70 kD.

Activity of cyclododecanone monooxygenase in the fractions was assayed by substrate-dependent NADPH oxidation. Typically, the background rate of NADPH oxidation (340 nm, 6.22 mM)in a mixture of 0.2 mL of enzyme+buffer (0.1 M glycine-NaOH, pH 8.8) without substrate was recorded using a spectrophotometer. One microliter of cyclododecanone (10 mM in n-propanol stock) was added, mixed with a loop of teflon-coated wire, and the $A_{340}$ trace was examined for cyclododecanone-stimulated NADPH oxidation.

The cyclododecanone monooxygenase enzyme was usually assayed by cyclododecanone-dependent NADPH oxidation as described previously. The product of the reaction, which is the lauryl lactone converted from cyclododecanone by the purified enzyme was also confirmed by GC/MS, as follows. Enzyme purified from the red agarose column was depleted of NADPH by repeated concentration and dilution cycles, using HB buffer and a Centricon-30 (Amicon). Cyclododecanone (800 mnol, 146 μg) in n-propanol was taken close to dryness in a 1 mL cuvette, diluted with 0.94 mL HB buffer, and supplemented with NADPH (36 μl of 11 mM stock). Twenty microliter of enzyme was added (5.8 mg/mL stock, determined using the Bio-Rad protein assay). After 20 min, the $A_{340}$ had decreased to about ¼ of its initial value. Additional NADPH (18 μl of 11 mM stock) was added at 20 min and at 1 h. At 90 min, the pH was adjusted to ~3 using the color of added bromophenol blue as a guide, and octadecane (146 μg) was added as an internal standard for GC/MS analysis. The sample was extracted with one mL of hexane (3×), dried with $MgSO_4$, and analyzed by GC/MS. HP5890 Gas Chromatographer was connected to a HP5971 mass-selective detector. DB-1 capillary column was used with 3 min hold at 75° C., increase to 220° C. at 10° C./min, increase to 300° C. at 20° C./min and 3.5 min hold at 300° C. Peaks were identified by comparison of their retention times and mass spectra with those of authentic standards. The sample contained lauryl lactone, cyclododecanone, and octadecane at ~1:0.08:1 area ratio, respectively. A parallel sample without enzyme contained cyclododecanone and octadecane only, at 0.75:1 area ratio.

Partial Amino Acid Sequencing of Cyclododecanone Monooxygenase Protein:

Protein from the red agarose column was separated on SDS-PAGE and electroblotted to PVDF membrane. The prominent 65 kD protein band was excised from the membrane and used for N-terminal amino acid sequencing by Edman degradation. N-terminal sequence of TTSIDREAL-RRKYAEERDKR (SEQ ID:14) was obtained. For internal sequence, protein was further purified by Reverse Phase-HPLC and 1 mg of protein was recovered from the HPLC purification. The recovered protein was dried, dissolved in 100 μl 70% formic acid containing 3 mg CNBr, and digested overnight. SDS gel loading buffer (50 μl) was added, plus enough 0.1 M Tris-Cl, pH 8, to bring the pH above 6. The volume was then reduced in a Centricon-10 concentrator (Amicon), and used for SDS-PAGE and electrdblotting for N-terminal sequencing of one of the most prominent CNBr fragment bands. The internal amino acid sequence of the ERIRARVDEIG (SEQ ID:15) was obtained and used to design degenerate primer for PCR amplification of portion of the cyclododecanone monooxygenase gene.

Example 3

Cloning Of Cyclododecanone Monooxypenase Gene From *Rhodococcus ruber* SC1

Reverse genetics strategy was employed for the cloning of cyclododecanone monooxygenase gene. Partial amino acid sequences were obtained from the purified enzyme as described above. The N-terminal amino acid sequence: TTSIDREALRRKYAEERDKR (SEQ ID NO:14) and the internal peptide sequence: ERIRARVDEIG (SEQ ID NO:15) were used to design degenerate PCR primers. Primer CDDK4: AARTAYGCNGARGARCGNGAYAA, where R=A or G, Y=C or T, N=A or C or G or T (SEQ ID NO:18) was derived from the N terminal sequence and primer CDDK10: CCDATYTCRRCNACNCKNGC, where D=A or G or T, Y=C or T, R=A or G, N=A or C or G or T (SEQ ID NO:19) was derived from the internal sequence. PCR was carried out as follows: one cycle of 94° C. for 5 min, 35 cycles of 94° C. for 1 min, 30° C. for 1 min and 72° C. for 30 sec followed by 1 cycle of 72° C. for 5 min. The PCR products obtained ranged from about 300 bp to 800 bp. The mixture of PCR products was cloned into the pCR2.1-TOPO cloning vector following manufacturer's instruction (Invitrogen, Carlsbad, Calif.). About 20 clones were sequenced using the standard M13 forward (−20) primer and the M13 reverse primer from the vector. One of the clones containing a insert of 556 bp had significant homology to cyclohexanone monooxygenase from Acinetobacter sp. NCIB9871 [Chen et al., *J. Bacteriol.* 170 (2), 781–789 (1988)] and steroid monooxygenase from *Rhodococcus rhodochrous* (Morii et al, AB010439). The deduced amino acid sequence of both ends of the insert DNA matched with the partial amino acid sequences (SEQ ID NO:14 and SEQ ID NO:15) previously determined from sequencing of the purified protein. The amino terminal methionine residue is cleaved thus, not found in the mature protein.

Example 4

Identification and Characterization of Cosmid Clones Containing Cyclododecanone Monooxygenase Gene From SC1 Library The cosmid library of Rhodococcus SC1 was screened using specific primers designed based on the sequence of the amplified N terminal DNA fragment of cyclododecanone monooxygenase gene from degenerate PCR. Two primers, C12 MO TOP: ATGCAGAGGAGCGGGACAAG (SEQ ID NO:20) and C12 MO BOTTOM: ACTTCGGTGTGGAA-CAGCGC (SEQ ID NO:21) amplified the 430 bp of N terminal fragment of cyclododecanone monooxygenase gene. The cosmid library was screened by PCR using C12 MO TOP and C12 MO BOTTOM primers. Six positive clones (D12D, E9F, O8E, O11G, S8C and T3C) were identified from two independent screens of total of 2000 clones. They all contain inserts of 35–40 kb spanning the cyclododecanone monooxygenase gene. Shot gun libraries of some of the cosmids were constructed and inserts were sequenced with pUC18 universal and reverse primers. Sequences of 400 clones were assembled using Sequencher 3.0 program and a contig of 10480 bp (SEQ ID NO:13) containing the cyclododecanone monooxygenase gene was formed.

Six ORFs (designated cddA, cddB, cddX, cddY, cddC and cddD) were identified from the 10480 bp contig (FIG. 2). BLAST (Basic Local Alignment Search Tool; Altschul, S. F., et al., (1993) *J. Mol. Biol.* 215:403–410; see also www.ncbi.nlm.nih.gov/BLAST/) searches were conducted for similarity to sequences contained in the BLAST "nr" database (comprising all non-redundant GenBank CDS translations, sequences derived from the 3-dimensional structure Brookhaven Protein Data Bank, SWISS-PROT protein sequence database, EMBL, and DDBJ databases). The sequences obtained were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI.

The sequence comparisons based on BLASTX analysis against the "nr" database are given below in Table 1 using Xnr BLAST algorithm.

TABLE 1

| Gene Name | Similarity Identified | SEQ ID base | SEQ ID Peptide | % Identity[a] | % Similarity[b] | E-value[c] |
|---|---|---|---|---|---|---|
| cddA | pir\|\|A28550 cyclohexanone monooxygenase [Acinetobacter sp.] | 1 | 2 | 30 | 46 | 3e-58 |
| cddB | emb\|CAA78842\| (Z15137) esterase A [*Streptomyces chrysomallus*] | 3 | 4 | 41 | 54 | 4e-78 |
| cddX | No hits found | 5 | 6 | | | |
| cddY | emb\|CAA18084.1\| (AL022121) hypothetical protein Rv3762c [*Mycobacterium tuberculosis*] 7 | 7 | 8 | 49 | 61 | e-169 |
| cddC | emb\|CAB02404\| (Z80226) adhB alcohol dehydrogenase [*Mycobacterium tuberculosis*] | 9 | 10 | 49 | 64 | e-105 |
| cddD | emb\|CAB46804.1\| (AL096811) putative aldehyde dehydrogenase [*Streptomyces coelicolor*] | 11 | 12 | 50 | 63 | e-127 |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that is expected in a search of a database of this size absolutely by chance.

BLAST results indicated that the sequence with the greatest homology to cddA encoding the monooxygenase was 30% identical and 46% similar to the gene published by Chen et al., *J. Bacteriol.* 170(2), 781–789(1988). The sequence with the greatest homology to cddB encoding the esterase was 41% identical and 54% similar to the gene published by Berger et al.,*J. Bacteriol.* 180 (23), 6396–6399 (1998). The sequence with the greatest homology to cddC encoding the alcohol dehydrogenase was 49% identical and 64% similar to the gene adhB identified from the complete genome sequence of *Mycobacterium tuberculosis* published by Cole et al., *Nature.* 393 (6685), 537–544 (1998). The sequence with the greatest homology to cddD encoding the aldehyde dehydrogenase was 50% identical and 63% similar to the gene identified from the *Streptomyces coelicolor* sequencing project at Sanger Centre.

Example 5

Production of 12-Hydroxyl Lauric Acid and 1,12 Dodecanoic Diacid by *E. coli* Cosmid Clones Six *E. coli* cosmid clones containing the 10 kb fragment including cyclododecanone monooxygenase gene were grown in M9 minimal medium supplemented with 0.4% glucose as the carbon source. Cells were grown at 30° C. with shaking to $OD_{600}$ of 0.2 and cyclododecanone dissolved in ethanol was added to each culture to a concentration of 250 mg/L. Cells were further incubated at 30° C. for 20 h. Control culture consisted of the host strain transformed with the SuperCos vector only was grown under the same conditions. Samples were frozen at ~80° C. and thawed at 37° C. Cells were pelleted and supernatants were passed through 0.22 μm disc filters. The filtered supernatants were acidified to pH 2 and extracted with methylene chloride. The methylene chloride residues after evaporation were derivatized by BSTFA (bis(trimethylsilyl) trifluoro acetamide) before injected onto the GC column.

All six cosmid clones produced a large peak with retention time around 24.8 min. Mass spectrometry analysis showed that the molecular weight of the compound in the peak was 360, corresponding to trimethylsilylated (TMS) 12-hydroxy lauric acid. In the vector control sample, this product peak was not detected. Furthermore, the cyclododecanone substrate peak at retention time around 19.7 min (molecular weight of 182) was detected in the vector control sample, but disappeared from the cosmid samples. Therefore, cyclododecanone was converted by the cosmid clones to 12-hydroxy lauric acid. In addition, a small peak at retention time around 25.6 min was also detected in some of the cosmid samples. Mass spectrometry analysis revealed the molecular weight of the peak compound to be 374, corresponding to the trimethylsilylated (TMS) 1,12-dodecanoic diacid (DDDA).

Quantitation experiment was performed by GC analysis with three representatives of the cosmid clones S8C, D12D O8E and the vector control using a DB-5 column (30 m×0.32 mm i.d. with a 1 μm coating, J & W Scientific). The temperature was programmed to begin at 50° C. for 5 min, ramp to 310° C. at 10° C./min and hold at 310° C. for 5 min. The injector was at 125° C. and the flame ionization detector was at 320° C. The retention time of the peaks was compared to that of the 12-hydroxy lauric acid or DDDA authentic standard. The quantitation result based on the peak area calculation was summarized in Table 2. Conversion percentage of cyclododecanone (CDDK) to 12-hydroxy lauric acid was high (56%), which suggested that the cyclododecanone monooxygenase cddA and the lauryl lactone hydrolase cddB were actively expressed in E. coli. The percentage for CDDK to DDDA conversion was only 1.7%, however, it was over 40 times higher than the background level in D12D and O8E (Table 2). One likely explanation was that the alcohol dehydrogenase and the aldehyde dehydrogenase encoded by cddC and cddD on S8C responsible for further convertion of 12-hydroxy lauric acid to DDDA were poorly expressed in E. coli.

TABLE 2

Production Of 12-Hydroxy Lauric Acid And DDDA From Cyclododecanone By E. Coli Cosmids

| Cosmid clones | 12-hydroxy lauric acid (% of conversion) | DDDA (% of conversion) |
| --- | --- | --- |
| Vetor control | 0 | 0 |
| S8C | 4900 μg (56.1%) | 160 μg (1.7%) |
| D12D | 2140 μg (24.1%) | 39 μg (0.04%) |
| O8E | 360 μg (4.1%) | 2 μg (0.021%) |

Example 6

Figure 3:
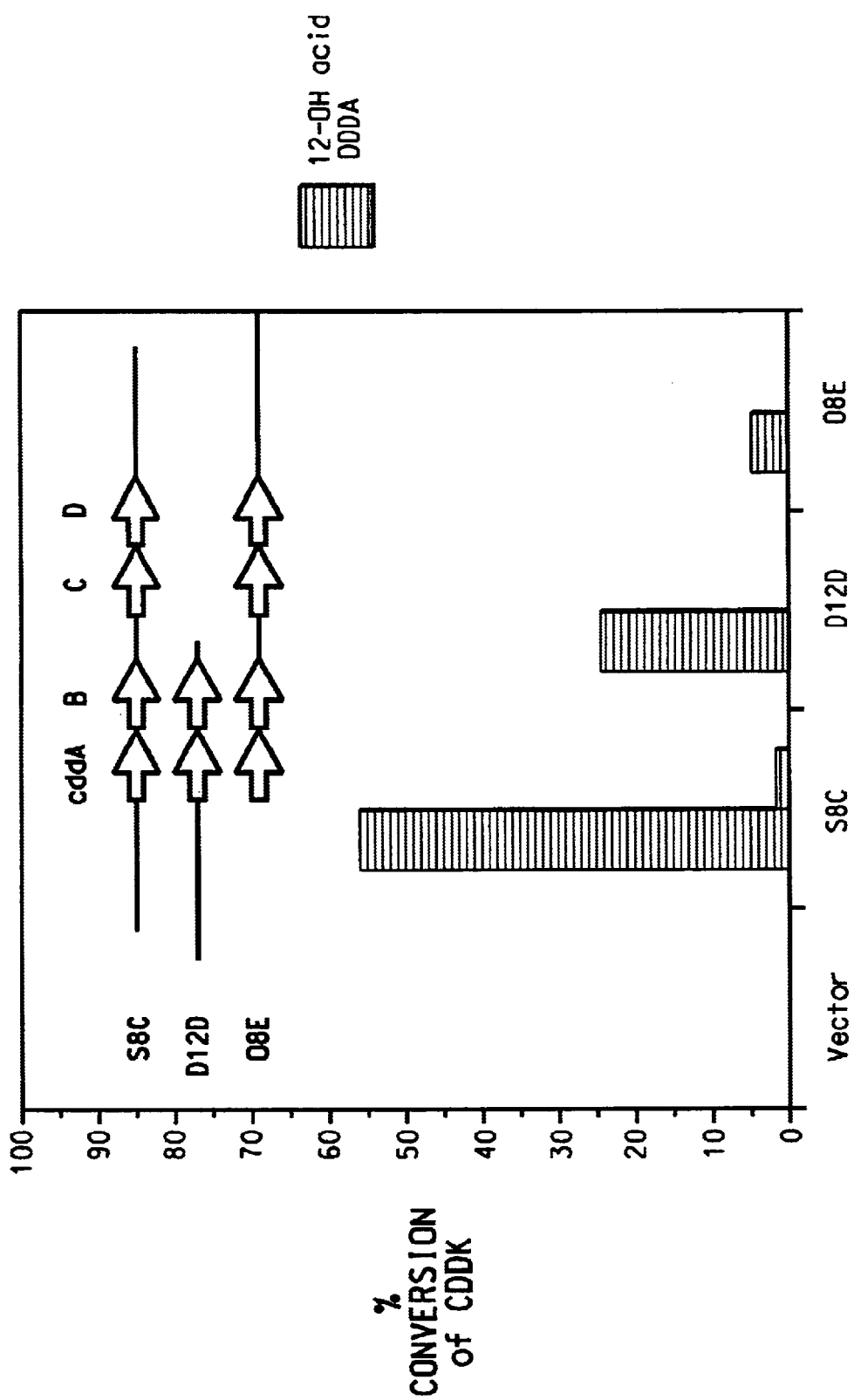
FIG. 3 is a diagram showing the amount of 12-hydroxy lauric acid and dodecanoic diacid produced from the recombinant E. coli cosmid clones.

Production of 12-Hydroxy Lauric Acid by E. coli Subclone Containing Only cddA and cddB Genes Since cosmids contain insert DNA about 35 kb, question arises as what subset of the genes on the cosmids contributed to converting cyclododecanone to 12-hydroxy lauric acid. Southern hybridization and PCR analysis suggested that most cosmids such as S8C contain the full 10 kb gene cluster and substantial upstream and downstream region. However, some cosmids contained only part of the 10 kb gene cluster. Cosmid D12D contains about 30 kb of upstream region plus only cddA and cddB gene from the cluster. The 3' end of the insert lay within the alcohol dehydrogenase sequence (cddC gene). Sequencing of the junction of D12D cosmid DNA using standard T7 primer on the vector mapped the end to be at 7346 bp, which contains only 51 bp of the N terminal region of the alcohol dehydrogenase gene (cddC). On the other hand, cosmid O8E contains intact cdd genes and about additional 25 kb downstream region, but very limited upstream region. Sequencing of the O8E 5' insert junction indicated that 515 bp upstream of cddA was present on O8E. The fact that lower amount of 12-hydroxy lauric acid was detected in O8E (Table 2) compared to S8C suggested that the limited upstream region of cddA and B on O8E might have affected the expression of cddA and B resulting in lower conversion to 12-hydroxy lauric acid. Taken together, the overlapping region of the D12D and O8E insert encodes only cddA and cddB genes. Both D12D and O8E produced 12-hydroxy lauric acid from cyclododecanone, which indicated that the only common genes cddA and cddB on the two clones were required for the conversion (FIG. 3).

To confirm that only cddA and cddB genes are required for conversion of cyclododecanone to 12-hydroxy lauric acid, these two genes with about 1 kb upstream region were subcloned onto pBluescript SK(+) vector. Primer KK1: CCCCAAGCTTGAACCCAGCCCCTGCAAGAT (SEQ ID NO:22) and primer KK2: GGACTAGTTCAGTTCGAG-CATCAGCCGCGG (SEQ ID NO:23) was used to amplify a 4243 bp fragment containing the cddA and cddB genes plus 1072 bp upstream and 101 bp downstream region. PCR product was digested with HindIII and SpeI and cloned into HindIII and SpeI sites of pBluescript SK(+) to construct pDCQ5. In pDCQ5, the cddAB genes was in the opposite orientation as the lacZ gene on the vector. A similar construct pDCQ6 was made using primer KK3: GGACTAGT-GAACCCAGCCCCTGCAAGAT (SEQ ID NO:24) and primer KK4: CCCCAAGCTTGTAGGAGAGTGCAC-CCTGGA(SEQ ID NO:25), which placed cddA and B genes in the same orientation as the lacZ gene. The fact that cosmid S8C produced 12-hydroxy lauric acid in E. coli suggested that either the promoter for cddA and cddB genes functions in E. coli or there is a fortuitous E. coli promoter present upstream of the cddA and B genes that drives the expression of the cddAB genes. The 1 kb upstream region on pDCQ5 or pDCQ6 presumably contains the promoter needed to express cddA and B genes in E. coli.

pDCQ5 and pDCQ6 were transformed into E.coli XL1BlueMR cells for bioconversion analysis. Two clones of each construct were chosen to grow in M9+glucose medium with cyclododecanone as substrate. Presence of 12-hydroxy lauric acid was assayed by GC/MS as described previously. 12-Hydroxy lauric acid was detected in both clones of pDCQ6, but not in either of the two clones of pDCQ5. DDDA was not detected in any clones of pDCQ5 or pDCQ6. Therefore, introducing only cddAB genes in the orientation as such on pDCQ6 conferred E. coli the ability to convert cyclododecanone to 12-hydroxy lauric acid. cddA gene encodes the cyclododecanone monooxygenase that converts cyclododecanone to lauryl lactone. cddB gene encodes lauryl lactone esterase that hydrolyzes the lauryl lactone to 12-hydroxy lauric acid.

Example 7

Production of Lauryl Lactone by Hydrolase Deletion Mutant

Conversion of cyclododecanone to lauryl lactone by cyclododecanone monooxygenase was demonstrated in vitro using purified enzyme as illustrated in Example 2. To demonstrate lauryl lactone could be produced and accumulated as an intermediate in vivo, *E. coli* strains containing only cyclododecanone monooxygenase gene cddA by deleting the downstream hydrolase gene cddB were constructed. The cddB hydrolase gene was deleted from pDCQ5 by isolating and self-ligating the 5.9 kb Klenow filled BglII-XbaI fragment containing the vector and cddA gene away from the 1.3 kb fragment containing cddB gene. The cddB esterase gene was deleted from pDCQ6 by isolating and self-ligating the 5.9 kb Klenow filled BglII-HindIII fragment containing the vector and cddA gene away from the 1.3 kb fragment containing cddB gene. The resulting constructs pDCQ7 and pDCQ8 were verified by restriction digests and retransformed into XL1BlueMR cells (Stratagene) for intermediates analysis by HPLC and GC/MS.

Two isolates of each construct pDCQ7 or pDCQ8 were grown in the presence of cyclododecanone as described previously. 100 μL of unconcentrated supernatants were taken for HPLC analysis. The pellets were extracted with 10 mL of acetonitrile and 100 μL of the pellet extracts were also analyzed by HPLC. The HPLC system used was a Hewlett-Packard 1100 series with a Photodiode array detector. Wavelength of 220 nm was used for detection. A Zorbax reverse phase C18 column (4.6 mm×25.0 cm) was purchased from Agilent Technologies (Palo Alto, Calif.). The column temperature was 30.0° C. and the flow rate was 1.0 mL/min. The isocratic mobile phase was 75% acetonitrile and 25% water. The retention time of the experimental samples were compared to that of the lauryl lactone authentic standard (Aldrich). Lauryl lactone was detected in the pellet extracts for both pDCQ8 clones, but not in any pDCQ7 clones, consistent with the expression interference observed in pDCQ5 (Example 6), from which pDCQ7 was derived. No lauryl lactone was detected in any supernatant.

Both supernatants and pellets were also analyzed by GC/MS as described previously. Supernatants were extracted with methylene chloride or ethyl acetate. The supernatant extracts and the acetonitrile pellet extracts were dried and concentrated in 1 mL of methylene chloride. One μl of underivatized sample was split injected and analyzed by GC/MS. Results confirmed those from the HPLC analysis. No lauryl lactone was detected in any of the concentrated supernatants, presumably due to hydrophobicity of the compound. Lauryl lactone and cyclododecanone were detected in pellet extracts of pDCQ8, which the putative native promoter was in the same orientation as the plac promoter on the vector. No lauryl lactone was detected in pellet extracts of pDCQ7, which the putative native promoter was in the opposite orientation as the plac promoter on the vector. Therefore, cyclododecanone monooxygenase was confirmed in vivo to convert cyclododecanone to lauryl lactone, and lauryl lactone was accumulated when the lauryl lactone hydrolase was genetically knocked out.

Example 8

Production of Different Chain Length Hydroxy Acids by Recombinant *E. coli* Clones Example 8 explores whether the cyclic substrates could be expanded to cyclic ketones of different chain length and whether corresponding hydroxy acids could be produced. S8C was grown as described above except that different cyclic ketones were added. Cyclohexanone (C6), cycloheptanone (C7), cyclooctanone (C8), cyclodecanone (C10), cycloundecanone (C11), cyclododecanone (C12), cyclotridecanone (C13) and cyclopentadecanone (C15) were added as substrates at 250 mg/L concentration. Identification of the corresponding hydroxy acids produced was performed by GC/MS analysis as described above. Large amount of corresponding hydroxy acids were detected from S8C grown in the presence of C11, C12 and C13 cyclic ketones. Medium level of 15-hydroxy acid was detected from C15 cyclic ketone grown cells. Small amount of hydroxy acids was detected from cells grown on C6 and C10 cyclic ketones. No hydroxy acid was detected when cells were grown on C7 or C8 cyclic ketones. The substrate range of the monooxygenase and esterase on the S8C appeared to favor long chain cyclic ketones (C>10). This correlated well with the growth substrate range (C 10–C15) of the *Rhodococcus ruber* SC1. The ability of *Rhodococcus ruber* SC1 to grow on cyclic ketones of C11 –C15 was likely due to the relatively broad substrate specificity of the single set of monooxygenase and esterase encoded on S8C clone (Table 3). It is possible that mixture of the large cyclic ketones may be used as substrates in a biotransformation to produce a mixture of long chain hydroxy acids or diacids for certain applications.

TABLE 3

Cyclic Ketones Specificity

| Cyclic Ketone Substrate | Growth of *Rhodococcus ruber* SC1 | Corresponding Hydroxy Acid Produced by *E. coli* Cosmids |
|---|---|---|
| C6 | − | +/− |
| C7 | − | − |
| C8 | − | − |
| C10 | + | +/− |
| C11 | + | ++ |
| C12 | + | ++ |
| C13 | + | ++ |
| C15 | + | + |

Example 9

Functional Expression of cddA Gene in *E. coli*

The initial purification of cyclododecanone monooxygenase from the native host of *Rhodococcus ruber* SC1 yielded only small amount of protein. It was decided to express the cddA gene from a strong *E. coli* promoter to increase protein yields.

Two primers, cddA-N: ATGACGACGAGCATCGACCG (SEQ ID NO:38)and cddA-C: TCAGCGGAAGGTGAGGCCGTCG (SEQ ID NO:39) were designed to amplify the 1812 bp full length of cddA gene from ATG start codon to TGA stop codon. The amplified cddA gene was cloned into pTrcHis2 TOPO TA cloning vector (Invitrogen, Carlsbad, Calif.) and transformed into TOP10 competent cells (Invitrogen). The ampicillin resistant transformants were first screened for the presence of the insert. They were also digested with EcoRI to check the insert orientation. Three clones designated pDCQ9, two of them (#2 and #5) in the forward orientation and the other one (#3) in the reverse orientation, were chosen for further protein expression analysis.

The cells were diluted from fresh overnight culture and growing in LB with ampicillin at 37° C. for about 3 hours. Each culture was divided into two tubes, one induced with 1 mM IPTG and one not induced. They were further incubated for 2 hours at 37° C. Cells from 1 mL of each sample were pelleted and resuspended in SDS sample buffer (BIO-RAD, Hercules, Calif.). The samples were boiled for 5 min and spun at 14,000 g for 10 min. The supernatants were loaded onto 8–16% gradient Tris-Glycine polyacrylamide gel (FMC BioProducts, Rockland, Me.). Overexpression of a protein at the expected molecular weight 65 kD was achieved with clone #2 and #5 under IPTG induction. The protein was also expressed at higher than basal levels in these two clones without IPTG induction, which is likely due to the leaky expression of the trc promoter under uninduced condition. On the other hand, no expression of this protein was observed with clone #3, which cddA gene was cloned in the wrong orientation relative to the trc promoter, under both induced and uninduced conditions.

For protein purification, 1-liter cultures of Top 10/pDCQ9 clone #2 were grown in 2.8 l Fembach flasks, in LB+100 µg/mL ampicillin, at 37° C. Enzyme production was induced by addition of 1 mM IPTG when the absorbance of the culture at 600 nm reached ~0.75, and growth was continued for four hours. Cells were collected by centrifugation, and stored at ~76° C. until needed. The purification was carried out at 4° C. Cells (~5 g wet weight) were suspended in HB buffer (50 mM Na-HEPES, pH 7.5, containing 10 mM 2-mercaptoethanol), to a volume of 40 mL. Phenylmethanesulfonyl fluoride (PMSF, 200 µl of 0.1 M in ethanol stock) was added, and the cells were passed through a French press at 16,000 psi. A second portion of PMSF was added, and cell debris was removed by centrifugation. The extract was applied to a 25 mL column of Q-Sepharose fast flow (Pharmacia) in HB, and the column was washed with 40 mL HB. The column was eluted with a gradient (250 mL total volume) from 0 to 0.7 M NaCl in HB. Active fractions, which were bright yellow in color, were pooled and diluted to 200 mL in HB. The pool was applied to a 60 mL column of Amicon Matrex Red A agarose, and followed with 60 mL of HB. Approximately 30 mg of homogeneous enzyme was eluted from the column with 200 mL 100 µM NADPH in HB. The yield of purified enzyme from the recombinant *E. coli* strain (6 mg of enzyme/g of cell paste) was much higher than the 20 µg of enzyme/g of cells yield from the native Rhodococcus strain. Activity of the enzyme purified from *E. coli* was also demonstrated using the cyclododecanone-dependent NADPH oxidation assay as described previously.

What is claimed is:

1. An isolated nucleic acid fragment encoding a lauryl lactone esterase enzyme selected from the group consisting of:
   (a) an isolated nucleic acid fragment encoding the amino acid sequence as set forth in SEQ ID NO:4,;
   (b) an isolated nucleic acid molecule that hybridizes with (a) under the following hybridization conditions: 6×SSC (1 M NaCl), 50% formamide, 1% SDS at 37° C., and a wash in 0.1×SSC at 60 to 65° C.; or
   (c) an isolated nucleic acid fragment that is completely complementary to (a), or (b).

2. An isolated nucleic acid molecule comprising a first nucleotide sequence encoding an enzymatically active lauryl lactone esterase of at least 386 amino acids that has at least 70% identity based on the Smith-Waterman method of alignment when compared to a polypeptide having the sequence as set forth in SEQ ID NO:4 or a second nucleotide sequence comprising the complement of the first nucleotide sequence.

3. An isolated nucleic acid fragment having at least 80% identity to the nucleic acid fragment selected from the group consisting of SEQ ID NO:3, SEQ ID NO:29, SEQ ID NO:30, and SEQ ID NO:31, and encoding an enzymatically active lauryl lactone esterase.

4. An isolated nucleic acid fragment having at least 90% identity to the nucleic acid fragment selected from the group consisting of SEQ ID NO:3 SEQ ID NO:29, SEQ ID NO:30, and SEQ ID NO:31, and encoding an enzymatically active lauryl lactone esterase.

5. The isolated nucleic acid fragment of claim 1 selected from the group consisting of SEQ ID NO:3, SEQ ID NO:29, SEQ ID NO:30, and SEQ ID NO:31, and encoding an enzymatically active lauryl lactone esterase.

6. A chimeric gene comprising the isolated nucleic acid fragment of claim 1 operably linked to suitable regulatory sequences.

7. A transformed host cell comprising a host cell and the chimeric gene of claim 6.

8. The transformed host cell of claim 7 wherein the host cell is selected from the group consisting of bacteria, yeast and filamentous fungi.

9. The transformed host cell of claim 8 wherein the host cell is selelted from the group consisting of Escherchia, Bacillus, Streptomyces, Pseudomonas, Salmonella, Acinetobacter, Rhodococcus, Aspergillus, Saccharomyces, Corynebacterium and Pichia.

10. A transformed host cell comprising the nucleic acid fragment of claim 1.

11. An isolated and purified *Rhodococcus ruber* comprising an endogenous gene encoding a protein as set forth by, SEQ ID NO:4, said *Rhodococcus ruber* having the ability to convert cyclododecanone to dodecanedioic acid under suitable growth conditions.

* * * * *